United States Patent [19]

Ohkawa et al.

[11] Patent Number: 5,308,751
[45] Date of Patent: May 3, 1994

[54] METHOD FOR SEQUENCING DOUBLE-STRANDED DNA

[75] Inventors: Tihiro Ohkawa, La Jolla; Robert L. Miller, San Diego, both of Calif.

[73] Assignee: General Atomics, San Diego, Calif.

[21] Appl. No.: 855,293

[22] Filed: Mar. 23, 1992

[51] Int. Cl.$^5$ .......................... C12Q 1/68; G01N 33/50
[52] U.S. Cl. .......................................... 435/6; 436/94; 435/91.2
[58] Field of Search .................... 435/6, 91.2; 436/94

[56] References Cited

U.S. PATENT DOCUMENTS

| | | | |
|---|---|---|---|
| 4,683,202 | 7/1987 | Mullis | 435/91 |
| 4,843,003 | 6/1989 | Henikoff et al. | 435/91 |
| 4,889,818 | 12/1989 | Gelfand et al. | 435/194 |
| 5,023,171 | 6/1991 | Ho et al. | 435/6 |
| 5,064,754 | 11/1991 | Mills | 435/6 |

OTHER PUBLICATIONS

Stallard, et al., Dideoxy sequencing of double-stranded DNA from poly(A)-extended 3'-ends, Anal. Biochem. (1987) 162:197–201.
Sanger et al., "DNA sequencing with chain-terminating inhibitors," *Proc. Natl. Acad. Sci. USA*, 74(12):5463–5467 (1977).
Mullis et al., "Specific enzymatic amplification of DNA in vitro: The polymerase chain reaction," *Cold Spring Harbor Symposia on Quantitative Biology*, 51:263–273 (1986).
Gyllensten et al., "Generation of single-stranded DNA by the polymerase chain reaction and its application to direct sequencing of the HLA-DQA locus," *Proc. Natl. Acad. Sci. USA*, 85:7652–7656 (1988).
Loh et al., "Polymerase chain reaction with single-sided specificity: Analysis of T cell Receptor & chain," *Science*, 243:217–220 (1989).
Gouvea et al., "Polymerase chain reaction amplification and typing of rotavirus nucleic acid from stool specimens," *J. of Clin. Microbio.*, 28(2):276–282 (1990).
McBride et al., "Automated DNA sequencing methods involving polymerase chain reaction," *Clin. Chem.*, 35(11):2196–2201 (1989).
Wallace et al., "A set of synthetic oligodeoxyribonucleotide primers for DNA sequencing in the plasmid vector pBR322," *Gene* 16:21–26 (1981).
Guo et al., "New rapid methods for DNA sequencing bases on exonuclease III digestion followed by repair synthesis," *Nucleic Acids Research*, 10(6):2065–2084 (1982).
Hattori et al., "Dideoxy sequencing method using denatured plasmid templates," *Analytical Biochemistry*, 152:232–238 (1986).
Lin et al., "An improved DNA sequencing strategy," *Analytical Biochemistry*, 147:114–119 (1985).
Chen et al., "Supercoil sequencing: a fast and simple method for sequencing plasmid DNA," *DNA*, 4(2):165–170 (1985).
Chi et al., "Modified method for double stranded DNA sequencing and synthetic oligonucleotide purification," *Nucleic Acids Research*, 16(21):10382 (1988).
Mehra et al., "Efficient mapping of protein antigenic determinants," *Proc. Natl. Acad. Sci. USA*, (List continued on next page.)

*Primary Examiner*—Margaret Parr
*Assistant Examiner*—David Schreiber
*Attorney, Agent, or Firm*—Fitch, Even, Tabin & Flannery

[57] ABSTRACT

A method for simultaneously sequencing both strands of a target DNA is provided. The method involves "shifting" one or both strands of the target DNA by addition or deletion of one or more nucleotides to one or both strands of the duplex to produce shifted DNA. Both strands of the shifted DNA duplex and the target DNA are sequenced and the sequences of the shifted and unshifted target DNA are compared. Since portions of the sequenced strands of the target and shifted DNA are identical, all or a portion of sequence of the target DNA can be determined.

18 Claims, 3 Drawing Sheets

OTHER PUBLICATIONS

83:7013-7017.

Mierendorf et al., "Direct sequencing of denatured plasmid DNA," *Methods in Enzymology,* 152, 152:556-562 (1987).

Kambara et al., "Real time automated simultaneous double-stranded DNA sequencing using two-color fluorophore labeling," *Bio/Technology,* 9:648-651 (1991).

Zhang et al., "Double stranded DNA sequencing as a choice for DNA sequencing," *Nucleic Acids Research,* 16(3):1220 (1988).

Strathmann et al., "Transposon-facilitated DNA sequencing," *Proc. Natl. Acad. Sci. USA,* 88:1247-1250 (1991).

Hsiao, K., "A fast and simple procedure for sequencing double stranded DNA with Sequenase," *Nucleic Acids Research,* 19(10):2787 (1991).

Kašper et al., "An improved double stranded DNA sequencing method using gene 32 protein," *Nucleic Acids Research,* 17(9):3616 (1989).

Bachmann et al., "Improvement of PCR amplified DNA sequencing with the aid of detergents," *Nucleic Acids Research,* 18(5):1309 (1990).

Tabor et al., "DNA sequence analysis with a modified bacteriophage T7 DNA polymerase," *Proc. Natl. Acad. Sci. USA,* 84:4767-4771 (1987).

Template S    Templates S and S⁻

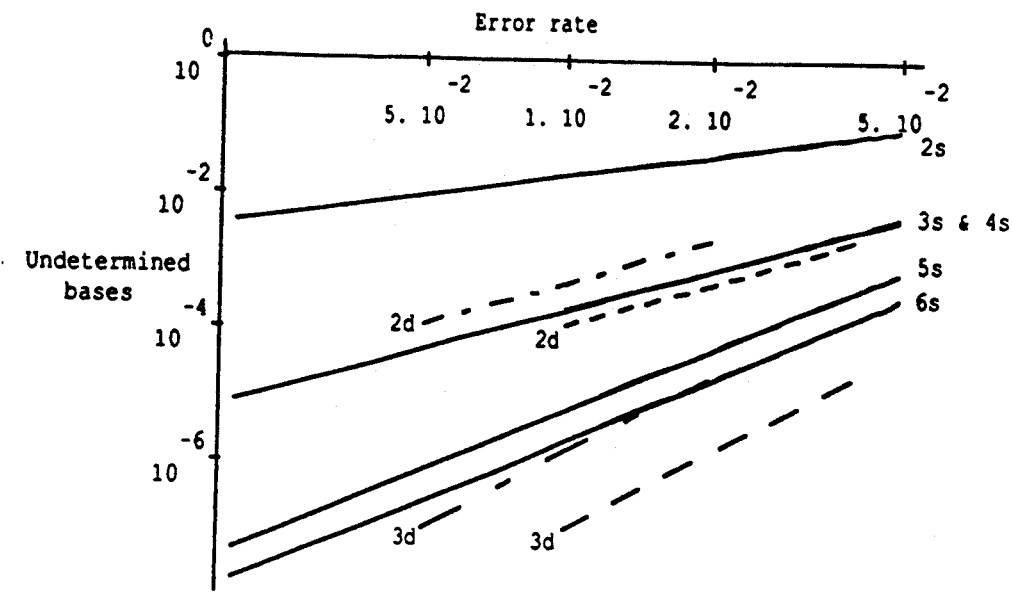
FIGURE 4
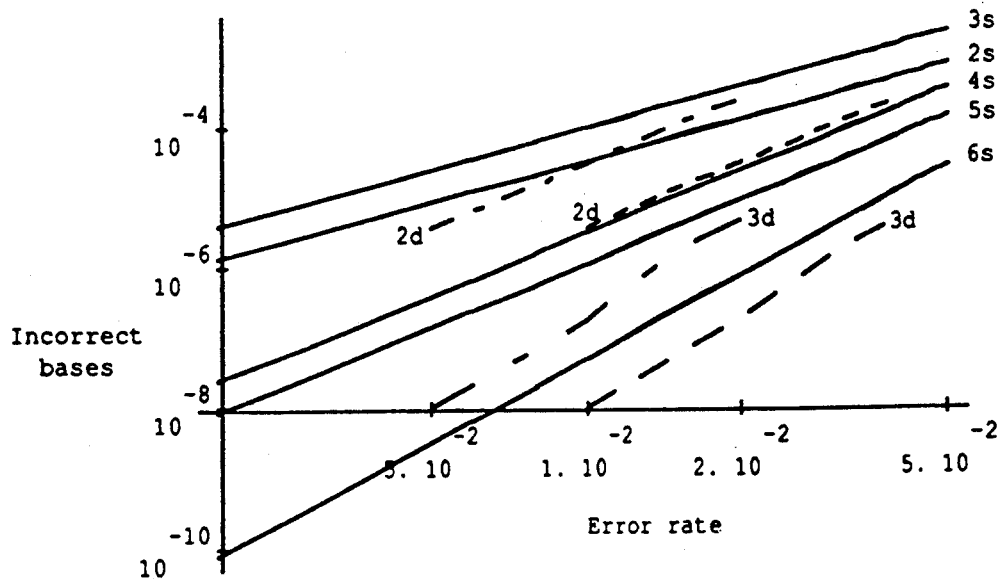

FIGURE 5

5' AAAATTTT-Target - AAAATTTT 3'
3' TTTTAAAA-Target'- TTTTAAAA 5'

↓ Denature, add primer, anneal primer

5' AAAATTTT-Target - AAAATTTT 3'       3' TTTTAAAA-Target'- TTTTAAAA 5'
3' TTTTAAAA-         - TTTTAAAA 5'     5' AAAATTTT            AAAATTTT 3'

↓ polymerize

5' AAAATTTT-Target - AAAATTTT 3'       3' TTTTAAAA-Target'- TTTTAAAA 5'
3' TTTTAAAA Target'- TTTTAAAA 5'       5' AAAATTTT-Target   AAAATTTT 3'

↓ Denature

5' AAAATTTT-Target - AAAATTTT 3'       3' TTTTAAAA-Target'- TTTTAAAA 5'
            +                                       +
3' TTTTAAAA-                           5' AAAATTTT-Target
            +                                       +
Target'- TTTTAAAA 5'                       AAAATTTT 3'

↓ Renature

5' AAAATTTT-Target - AAAATTTT 3'
3' TTTTAAAA-Target'- TTTTAAAA 5'
+
5' AAAATTT-Target
          Target'- TTTTAAAA 5'
+
5' AAAATTTT-Target 3'
3' TTTTAAAA
+
5' AAAATTTT-Target - AAAATTTT 3'
3' TTTTAAAA              TTTTAAAA 5'
+
3' TTTTAAAA-Target'- TTTTAAAA 5'
5' AAAATTTT              AAAATTTT 3'
+
Target'- TTTTAAAA 5'
         AAAATTTT 3'
+
other renaturation products

METHOD FOR SEQUENCING DOUBLE-STRANDED DNA

FIELD OF THE INVENTION

The present invention is directed to methods for simultaneously sequencing both strands of a DNA fragment. The methods permit errors in sequences to be detected.

BACKGROUND OF THE INVENTION

DNA sequencing methods are important and powerful tools in the molecular biologist's repository of techniques for assessing and understanding gene expression and regulation. Methods for sequencing DNA molecules include chemical degradation sequencing (Maxam et al. (1977) *Proc. Natl. Acad. Sci. USA* 74: 560, see, also, Ambrose et al. (1987) *Methods Enz.* 152: 522) and chain termination sequencing (Sanger et al. (1977) *Proc. Natl. Acad. Sci. USA* 74: 5463). The Maxam-Gilbert sequencing method is a degradative method that relies on specific cleavage of DNA fragments. A fragment of DNA, which is radiolabeled at one end, is partially cleaved in five separate chemical reactions. Each reaction is specific for a type of base or a base so that five populations of labeled fragments of differing lengths are generated. The populations of fragments are resolved by polyacrylamide gel electrophoresis (PAGE).

The chain termination or Sanger method, which is presently the preferred method for sequencing DNA, relies on a DNA synthesis. Single-stranded DNA is used as a template and labeled primers are used to initiate formation of complementary strands. The synthesis reaction is run in the presence of the four deoxynucleotides (dNTPs), dATP, dTTP, dCTP and dGTP and one of the four dideoxynucleotides (ddNTPs), ddATP, ddTTP, ddCTP, and ddGTP. The complementary strands are prematurely terminated along the chain by addition of dideoxynucleotides to the growing chains. By starting with four reaction mixtures, which each contain one of the four ddNTPs, sets of strands terminating in A, C, G and T are generated. Each reaction mixture is electrophoresed in one lane of a polyacrylamide gel that resolves fragments that differ by a single base in length.

These methods are primarily designed for sequencing single-stranded DNA, which is produced by denaturing the DNA and separating the single strands, or by other methods, such as cloning into single-stranded phage vectors. These sequencing methods rely on reactions that produce an array of fragments that differ in length by a single base and terminate in an identifiable base. The fragments are resolved by size using PAGE and are detected using a label, such as a radioisotope. Because the resolution of bands on an electrophoretic gel decreases exponentially as the length of the DNA fragments increase, these methods only permit DNA fragments of up to about 300 to 400 nucleotides to be sequenced.

Before sequencing, sufficient quantities of the single strands can be generated by cloning and replicating the target DNA in a bacterial host using a suitable vector, such as the single-stranded filamentous phage vectors, M13 (see, e.g., Messing (1983) *Methods Enzymol.* 101: 20), and other phage vectors (see, e.g., Barnes et al. (1983) *Nucl. Acids Res.* 11: 349-368; Dente et al. (1983) *Nucl. Acids Res.* 13: 1645-1655; Laughton et al. (184) *Nature* 310: 25-31). Sequencing can then be effected using a so-called universal primer that is complementary to the vector near the site at which the target DNA is inserted.

The target DNA can also be amplified using the polymerase chain reaction (PCR) (see, e.g., Mullis et al. (1986) *Cold Spring Harbor Symp. Quant. Biol.* 51: 263; U.S. Pat. No. 4,683,202 to Mullis et al.), which results in an amplified concentration of the duplex target DNA. A number of methods have been used to generate single-stranded templates directly from PCR for subsequent sequencing. For example, radio-labeled primer that is specific for only one strand may be used. Alternatively, PCR may be run under conditions such that one primer is at limited concentration. Once the primer that is at the limited concentration is exhausted, the second strand is amplified at a linear rate through succeeding cycles (Gyllenstein et al. (1988) *Proc. Natl. Acad. Sci.* 85: 7652; Mihilovic et al. (1989) *BioTechniques* 7: 14).

There are numerous sequencing strategies in use. The selected strategy depends upon the purpose for which the DNA is sequenced and the amount of information available about the DNA prior to sequencing. For example, if the target DNA is sequenced in order to confirm that a particular mutation has been introduced into the DNA, it may only be necessary to sequence a small region of DNA. If the DNA fragment is an unknown gene or portion of a gene for which a sequence must be accurately determined, then it may be necessary to sequence the entire fragment. Because the sizes of fragments that can be sequenced are limited to about 400 bases, DNA fragments longer than this size must be cleaved. Cleavage may be random, by subcloning segments of the target DNA. The subcloned fragments, which include overlapping fragments, are then sequenced, and ordered using a computer program see, e.g., Staden (1986) *Nucl. Acids Res.* 14: 217). Alternatively, the DNA may be systematically subcloned by generating and sequencing overlapping or nested mutants or by other ordered approaches.

The Sanger chain termination method and other sequencing methods rely on the use of single-stranded template by cloning the target DNA into single-stranded phage vectors. The use of plasmids as vectors for the target DNA, however, is preferred over the use of phage DNA for reasons, which include the variety of available plasmids, the ease with which plasmids are manipulated, and the greater stability of inserted DNA in plasmids compared to phage vectors. Consequently, methods for sequencing in which the target DNA is cloned into plasmid DNA, rather than into a single-stranded phage DNA (see, e.g., Wallance et al. (1981) *Gene* 16: 21-26; Guo et al. (1982) *Nucl. Acids Res.* 10: 2065-2084; Vieira et al. (1982) *Gene* 19: 259-268) have been developed.

These methods are designed to only sequence one strand of the target DNA at a time (see, e.g., Chen et al. (1985) *DNA* 4: 165-170; Hattori et al. (1986) *Anal. Biochem.* 152: 232-238; Mierendorf et al. (1987) *Methods Enzymol.* 152: 556; Mehra et al. (1986) *Proc. Natl. Acad. Sci, U.S.A.* 83: 7013-7017). Use of double-stranded DNA, however, avoids the subcloning or isolation of single-stranded DNA fragments, which are used for the dideoxy chain terminator sequencing reactions. The use of double-stranded DNA, however, had been limited because of the poor template quality of denatured duplex DNA. As a result, these methods had not provided as accurate sequence data as provided by methods in which the DNA is cloned into a single-stranded vector.

Recently, the problems associated with template quality have been solved by the development of methods that use plasmids that include sites, adjacent to both complementary strands of the inserted DNA, to which strand-specific primers may be efficiently hybridized. By virtue of these methods each of the single strands of double-stranded DNA can be sequenced directly from plasmid DNA without prior subcloning into phage vectors (see, e.g., Chen et al. ((1985) *DNA* 4: 165-170 and Chi et al. (1988) *Nucl. Acids Res.* 16: 10382). A strand specific synthetic primer is annealed to covalently closed circular DNA, which has been denatured by heat or alkali, before proceeding with dideoxy sequencing reactions. Alternatively, the primer can be annealed to open circle double-stranded plasmid DNA, which has been denatured by alkali, as a template (see, Hattori et al. ((1986) *Anal. Biochem.* 152: 232-238). The double-stranded DNA is denatured with alkali or heat prior to sequencing using the Sanger method, which is performed at 37° C. or higher. The use of different "forward" and "reverse" primers, which are each complementary to the lac Z sequences adjacent to the EcoRI site in λgt11, for separately sequencing each strand of DNA that has been cloned into λgt11 has also been described (see, Mehra et al. (1986) *Proc. Natl. Acad. Sci, USA* 83: 7013-7017).

Plasmids with oppositely oriented promoter regions, which are used in methods which involve transcription, are also used as vehicles for target DNA which is to be sequenced. Each promoter region serves as a distinct specific priming site for sequencing the inserted DNA. Such plasmids are commercially available. For example, the twin promoter plasmid pGEM TM contains the bacteriophage SP6 and T7 RNA polymerase promoters in opposite orientations (Mierendorf et al. (1987) *Meth. Enzymol.* 152: 556-562).

Although methods for sequencing of single-stranded are superior to those for sequencing double-stranded DNA, unless both strands are sequenced, such methods do not allow for detection of errors generated in the sequencing process nor correction of those errors, since only the information from a single strand is available. Sequencing errors arise from a number of sources, including the quality of the template DNA and the type of DNA polymerase used. For example, premature dissociation of the DNA polymerase from the template before the terminating ddNTP is introduced into the replicating fragment is a common cause of error in the Sanger method. Each DNA polymerase has a characteristic tendency to dissociate, which is measured by the processivity, the average number of nucleotides synthesized before the enzyme dissociates from the template. DNA polymerase I of *E. coli* has an average processivity of 10-50, SEQUENASE TM or SEQUENASE TM 2.0 has a processivity of approximately 2000 and 3000 respectively, and Taq DNA polymerase has a processivity of greater than 7600 nucleotides. (Sambrook et al. (1989) *Molecular Cloning: A Laboratory Manual*, 2nd Ed., Cold Spring Harbor Laboratory Press, Cold Spring Harbor Laboratory Cold Spring Harbor, N.Y., at p. 13.8). Thus *E. coli* DNA polymerase tends to generate a higher background of fragments because the enzyme often dissociates from the template before the terminating ddNTP is incorporated. Using a polymerase that terminates prematurely or using a damaged template, which produces a high "background" of inaccurate oligonucleotides, results in erroneous sequencing data. Additional sources of error include sequence anomalies, such as regions of dyad symmetry, which produce overlapping bands on a gel, and the formation of secondary structures between oligonucleotides or within an oligonucleotide, which causes the oligonucleotides to migrate improperly, which in turn produces compressed bands on a separating gel.

Because double-stranded DNA is composed of complementary strands, the accuracy with which a sequence is determined can be improved by sequencing both strands of DNA. It has been estimated (Sambrook et al. (1989) *Molecular Cloning: A Laboratory Manual*, 2nd Ed., Cold Spring Harbor Laboratory Cold Spring Harbor, N.Y.) that an accuracy of 0.1% can be achieved by sequencing a strand and its complement and resolving all discrepancies between the strands. Some methods for simultaneously sequencing both DNA strands have been developed. Thus far, these methods are less convenient than those for sequencing single-strands.

For example, one method for sequencing double-stranded DNA (Guo et al. (1982) *Nucl. Acids Res.* 10: 2065-2084) includes the steps of cleaving a plasmid that contains the inserted DNA with a restriction enzyme, which cuts at only one site to produce a linear molecule having either recessed 3' ends or blunt ends, followed by controlled digestion with exonuclease III to produce shortened 3' ends and long 5' ended single strands. In one variation of the method, samples of the digested molecules are removed at regular time intervals as exonuclease reaction proceeds, and are pooled. In a second variation, the reaction is stopped after a predetermined time. Labeled nucleotides are then incorporated into the 3' termini of the exonuclease III-digested DNA to produce molecules that serve as template-primer systems in which the shortened strands with the 3' single-stranded ends serve as primers. In the first variation of the method, each of the four [$\alpha$-$^{32}$P] dNTP are added to one of four reactions. In the second variation, the four ddNTPs and the four dNTPs are used in each of four reactions with one [$\alpha$-$^{32}$P] dNTP added to each reaction. In both variations of the method, the linearized plasmid is labelled at both ends. Upon digestion with a second restriction enzyme that cuts the fragments asymmetrically, two families of labeled fragments are produced. When these are run on a separating gel, the sequences of the strands of DNA from each of the 3' ends up to the points at which exonuclease III cleavage ended can be read. This method, however, requires a plasmid that has appropriate restriction sites so that asymmetric cleavage can be effected and also relies on the uniformity of the rate of digestion with exonuclease III. Other drawbacks include difficulties that arise from sequencing DNA that contains runs of identical bases, particularly using the first variation, and the appearance of extraneous bands, when using the second variation. In addition, although this method sequences both strands of double-stranded DNA, it does not readily provide overlapping sequence data. Rather, part of the target DNA sequence is obtained from one end of the fragment and another part of the sequence is obtained by sequencing the other end of the fragment.

Another method (Kambara et al. (1991) *Biotechnology* 9: 648-651) for simultaneously sequencing both strands of duplex DNA uses the Sanger chain termination method in conjunction with differential fluorophore dye labelling. In one variation, forward and reverse primers are labeled with two different fluorophore dyes. DNA fragment families ending in the four different base species are collected and placed in four different electrophoretic tracks. The fragments originating from the forward direction can be distinguished from the fragments originating from the reverse direction by the fluorescence pattern from each dye. This method, however, requires the prior labelling of terminators or primers with fluorescent dyes, a laser as an excitation light-source, and a multi-color detector attached to an automatic sequencer.

Thus, although it is desirable to sequence both strands of a DNA molecule in order to accurately determine the sequence, methods for simultaneously sequencing both strands of a DNA fragment have not as yet been perfected so that double-stranded sequencing can be performed as conveniently and routinely as single-stranded sequencing.

Therefore, it is an object of this invention to provide a straightforward efficient method for simultaneously sequencing both strands of a DNA fragment. It is also an object of this invention to provide a method for detecting and correcting sequencing errors.

SUMMARY OF THE INVENTION

Methods for accurately determining the sequence of a double-stranded DNA fragment by simultaneously sequencing both strands of the DNA are provided. In accordance with these methods, one portion of a sample of target DNA is modified by addition or deletion of one or more nucleotide bases to one or both strands to produce shifted DNA. Alternatively, the target DNA may also be modified such that two portions of DNA are prepared. The DNA in one portion differs from the DNA in the other portion in the length of one or both strands. Both strands of the shifted DNA and of the unmodified or modified target DNA are then sequenced to yield data sets of alternative bases for each position.

In embodiments in which sequencing is effected using a DNA polymerase, the DNA may effectively be shifted by priming the reactions with primers of different lengths. Whatever method of modification is selected two data sets of sequence information are generated. One data set is referred to as shifted with respect to the other. The resulting data sets for the sequences of the strands of the shifted and target DNA are compared and the sequence of all or a portion, which portion includes a larger portion of the target DNA than is included in the shifted DNA, of the sequence of the target DNA is determined. These methods, thus, generate sufficient information with respect to the nucleotide sequence of the target DNA to completely determine, all or a portion of the sequence of the target DNA. The determined portion includes more sequence of the target DNA than is present in the shifted DNA.

In preferred embodiments, the shifted DNA includes a sufficient portion in common with the target DNA to permit the entire sequence of the target DNA to be determined. In addition, in certain embodiments, because the target DNA is simultaneously sequenced from both ends, the methods permit longer fragments of DNA to be sequenced than methods in which single-strands are sequenced. Preferred embodiments of the methods should provide a means to sequence DNA fragments up to about 800 nucleotides in length.

In addition, in certain preferred embodiments in which the entire sequence of the target DNA is deduced, the methods herein also provide a means for detecting errors and correcting errors generated in the sequencing process.

In practicing the methods, a portion of the target DNA is shifted and both the shifted and unshifted target DNA are sequenced to yield a data set $g_0$ of alternative bases for each base pair of the target DNA and a data set $g_1$ of alternative bases for each base pair of the shifted DNA. The shifted DNA molecule differs from the modified or unmodified target DNA molecule by the addition or deletion of bases from one or both strands of the duplex. Upon sequencing the shifted DNA, a second data set $g_1$ is generated. Since the shifted DNA includes all or a portion of the DNA in the target DNA, comparison of $g_0$ with $g_1$ permits all or a portion of the DNA sequence of both strands of the target DNA to be determined. In particular, if a single base on the target or shifted DNA is known, and the shifted DNA includes at least about 50% of the target DNA, the entire DNA sequence of the target DNA can be deduced. If the shifted DNA includes more than at least about 50% of the target DNA, not only may the entire sequence of the DNA be determined, but sequencing errors may be detected. If the shifted DNA includes about 100% of the target DNA, the method permits error detection, and in certain embodiments, error correction.

Sequencing may be done by any method known to those of skill in the art from which a data set of alternative bases for each location on the double-stranded DNA is generated. In preferred embodiments, the DNA is sequenced using the chain-terminating dideoxynucleoside triphosphate Sanger technique producing four sets of oligonucleotide fragments, which are separated on a separating gel.

The shifted DNA may be prepared by any method known to those of skill in the art, which results in a DNA fragment in which one or both strands is longer or shorter than the strands of the target DNA. For example, inserting the DNA into a plasmid between oppositely oriented promoters and the subsequent use of primers of different lengths that are complementary to all or a portion of the promoter sequences provides a means to generate sequence data from both unshifted and shifted DNA. In preferred embodiments, the shifted DNA includes one strand identical to the target DNA and one strand that is longer or shorter by a known number of bases. In addition, the shift is effected so that at least one base on the shifted or unshifted strand is known. In other embodiments, the shifted DNA may be generated by treating the target DNA with a restriction endonuclease that cuts, preferably, in one location, in the target DNA. The restriction fragments are then separated and both strands of one or more restriction fragments are simultaneously sequenced and both strands of the target DNA are simultaneously sequenced.

In preferred embodiments, in which both strands are sequenced as means to obtain an error free sequence, the shifted DNA contains one strand that is identical to or longer than one strand in the target DNA and one strand that is longer than the other, unshifted strand, by an even number of bases.

An algorithm for unraveling the DNA sequence is also provided. This algorithm may be modified to accommodate various shifts of the target DNA that may be performed. Based on the disclosure herein, other algorithms for deducing the DNA sequence of the target DNA from the data sets may be developed by those of skill in the art.

A method for amplifying a sample of double-stranded DNA for which the sequence is completely unknown is also provided herein. This amplification method also provides means to amplify the target DNA and to produce and amplify shifted DNA. This method may be used in conjunction with the method of sequencing either to produce shifted DNA or to produce a sufficient amount of target or shifted double-stranded DNA for sequencing.

According to the amplification method, a single or double-stranded tail of known sequence, preferably a homopolymer or palindromic sequence of a length sufficient to serve as a primer for the polymerase chain reaction, is added to a double-stranded DNA fragment, and the strands are denatured. The ligase used in adding the tail is inactivated by chemical or physical methods, primers that are complementary to the tails are added, a DNA polymerase and nucleoside triphosphates are added, and the DNA is amplified by synthesizing the second strand of the DNA by addition of a polymerase and deoxynucleoside triphosphates under appropriate conditions.

Kits for practicing the amplification and sequencing methods are also provided.

BRIEF DESCRIPTION OF THE DRAWINGS

FIG. 3 is a graphical representation of the fraction of undetermined bases versus the error rate for the sequencing of 2-6 single strands and the sequencing of 2 and 3 double strands. The equally spaced dashed lines correspond to the reading error model while the unequally spaced dashed lines correspond to the error rate applied to each base of an individual gel reading. Each gel corresponds to a pair of alternative bases. In the reading error model, when an error occurs, the gel reading is randomly replaced by one of the other nine possible gel readings.

FIG. 4 depicts the fraction of incorrect bases versus the error rate for the sequencing of 2-6 single strands and sequencing of 2 and 3 double strands. The equally spaced dashed lines correspond to the reading error model and the unequally spaced dashed lines correspond to the error rate applied to each base of an individual gel reading.

FIG. 5 outlines the steps in the amplification method in which palindromic tails are added to the target DNA to produce shifted DNA and the target DNA and shifted DNA are amplified. If ligase is added following the polymerization and denaturation step, complete templates can be regenerated and the method will exponentially amplify the shifted target DNA.

DETAILED DESCRIPTION OF PREFERRED EMBODIMENTS

Definitions

Figure 1:
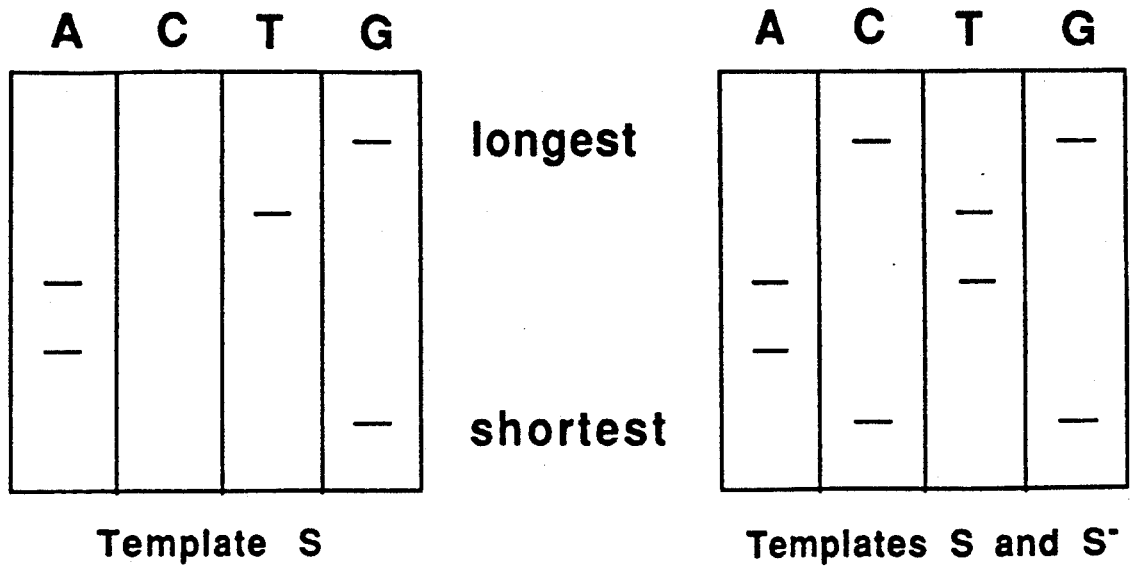
FIG. 1 shows a representation of gels for a single strand chain termination sequencing of S and for a double strand sequencing of S and $S^-$. $S^-$ is complementary to S.

Unless defined otherwise, all technical and scientific terms used herein have the same meaning as is commonly understood by one of skill in the art to which this invention belongs. All patents and publications referred to herein are incorporated by reference herein.

As used herein, target DNA refers to the DNA fragment of interest that is sequenced. In general, the target DNA may be of any length, but is preferably less than about 600 to 800 nucleotides, and most preferably less than about 600 nucleotides. DNA fragments for sequencing that are substantially longer than the preferred length may be cleaved using any method known to those of skill in to the art into small fragments of the desired length.

As used herein, the term shifted DNA refers to DNA that has been modified by the addition or deletion of nucleotide bases to or from one or both strands of DNA such that the resulting DNA fragment contains at least one single strand that differs in length by one or more nucleotides from the unmodified DNA fragment. Shifting is effected by selectively adding or deleting bases from one or both strands of a DNA fragment, such as by cutting a fragment with a restriction endonuclease that generates identifiable fragments, by selectively adding or deleting one or more nucleotide bases to one or both termini of one or both of the complementary strands of the double-stranded DNA, such that the two strands are subsequently of different lengths.

Any method the results in two portions of DNA that include overlapping regions may be used to produce shifted DNA. For example, in embodiments in which the DNA is sequenced by a method that requires priming, shifting may be effected during the sequencing reactions by priming the sequencing reactions for each double-stranded sequencing event with primers of different lengths. Such primers are herein referred to as shifted primers. By priming each sequencing reaction with primers of different lengths, the resulting sequencing reactions produce data sets that are effectively shifted.

As used herein, simultaneously sequencing both strands of a DNA molecule means that, whatever method is used to sequence the DNA, it is simultaneously applied to both strands of the duplex. Any method of sequencing that generates data sets of pairs of nucleotides as defined herein may be used to sequence the duplex. In preferred embodiments, the Sanger chain termination method is used.

As used herein, $g_n$ refers to a data set that is generated by simultaneously sequencing both strands of a shifted duplex DNA fragment. The data set $g_n$ is defined by a series of alternative nucleotides, represented $\{\{a_1, b_1\}, \{a_2, b_2\}, \ldots \{a_i, b_i\} \ldots \{a_x, b_x\}\}$. Both x and n are integers from 1 up to any number. x refers to the number of the bases on the single strand from the 5' end and n refers to the data set number. The expression $g_0$ refers to the data set generated by simultaneously sequencing both strands of the target DNA. In preferred embodiments, the number of bases by which one strand of shifted DNA is shifted relative to the target or modified target DNA, typically has a value that is less than about 10 and is preferably an even integer less than bbout 6, and x is preferably less or equal to about 600 and is preferably less than or equal to about 400. In certain embodiments, x can be as high as about 800.

As used herein, unless noted otherwise, the position on each strand is numbered from the 3' end to the 5' end. When both strands of DNA are sequenced simultaneously, it is not possible to uniquely assign a base pair to a particular strand, instead a data set with two alternative bases at each position, $\{a_i, b_{x-i+1}\}$, on each of the strands is generated. If the strands have an identical base at a position, the base is identical, $b_{x-i+1}=a_i$, and the particular point in the data base is assigned identical identifying bases.

As used herein, the term "oligonucleotide" refers to a single-stranded molecule of two or more deoxyribonucleotides (or ribonucleotides).

As used herein, the term "primer" refers to an oligonucleotide complementary to a portion of the target DNA. Upon annealing to the target DNA, the primer-target duplex serves to prime DNA synthesis in the presence of an appropriate DNA polymerase, deoxynucleoside triphosphates, and suitable conditions. The oligonucleotide primer may be synthesized or obtained from naturally occurring sources such as restriction digests of known plasmids. In order to simultaneously sequence both strands of a double-stranded DNA molecule, primers must be provided to anneal with sequences adjacent to or at the 5' termini of both complementary strands. Shifted primers refers to primers of different lengths.

As used herein, the term "sequencing event" refers to each time both strands of a target DNA duplex or shifted DNA duplex are simultaneously sequenced. The first sequencing event of the method provided herein produces the original data set of alternative base pairs $g_0$. The second sequencing event produces the shifted data set of alternative base pairs $g_1$. The third sequencing event produces the second shifted data set of alternative base pairs $g_2$, and so on.

As used herein a shifted data set of alternative base pairs refers to the data set that is produced by sequencing DNA that is shifted with respect to the target DNA or to the modified target DNA. A shifted data set may be generated by methods that generate data sets of alternative base pairs that are shifted with respect to another set of such pairs. Such methods include, but are not limited to, the use of shifted primers to sequence the target DNA.

As used herein, the expression "tail" refers to a duplex DNA fragment that has been added to a target DNA at both termini. This may be accomplished by any method known to those of skill in the art and by the methods described herein. Tails may be of any length sufficient, to serve as a primer. Preferably the tails have a sequence of from about 8 to 50 nucleotides.

As used herein, the expression "palindromic tail" refers to a duplex tail that has a nucleotide sequence that is a palindrome. Thus, there is a point in the tail from which the nucleotides in the 5' direction have the complementary sequence to those in the 3' direction. A palindromic sequence forms a mirror image with its complementary sequence. Both strands of a DNA fragment tailed with palindromic tails can be primed for DNA synthesis, for example for chain termination sequencing or PCR, by a single oligonucleotide.

As used herein, a homopolymeric tail, refers to a tail in which one strand contains a string of one single nucleotide base and the complementary strand is a polymerized strand of the complementary base.

The information content of double-stranded DNA and methods for increasing the available information When both strands of a double-stranded DNA fragment are simultaneously sequenced, a great deal of information is produced about each sequence, but this information is insufficient, other than in the case in which the sequence of the fragment is a palindrome, to uniquely determine the sequence of the DNA fragment. To the extent the DNA is a palindrome, the mirror image nucleotide bases can be unambiguously identified. The more the sequence of a DNA molecule differs from a palindrome, the less information about the sequence is obtained.

In general, sequencing methods sequence each strand of duplex DNA from the same direction. If both strands are simultaneously sequenced, unless a particular location, determined from either the 5' or 3' end of the strands, has the same base on both strands, the resulting sequence is a set of data pairs of alternative bases, $g_0$, for each location with respect to the 5' (or 3') end of the target DNA. Thus, to the extent the sequence of the target DNA differs from a palindrome, when the strands of a target DNA fragment are simultaneously sequenced, the resulting data cannot unambiguously assign a particular base to each strand. In order to assign a particular base to each strand additional information is necessary.

The methods herein provide means to readily obtain such information and to thereby completely or partially obtain the sequences of both strands of a duplex DNA molecule. The information is obtained by simultaneously sequencing both strands of a second double-stranded DNA molecule that is shifted with respect to the target DNA. The shifted data is obtained by any means that effectively generates data that would be produced by sequencing a DNA molecule that differs from the target DNA molecule by the addition or deletion of bases from one or both strands of the duplex. Upon sequencing the second shifted DNA, a second data set $g_1$ is generated. Since the shifted DNA includes all or a portion of the DNA in the target DNA, comparison of $g_0$ with $g_1$ permits all or a portion of the DNA sequence of both strands of the target DNA to be determined.

The methods herein, thus, provide sequence information by simultaneously sequencing both strands, a and b, of a double-stranded DNA molecule and comparing the resulting data set, $g_0$, with the data set, $g_1$, obtained by simultaneously sequencing both strands of a second DNA fragment that includes all or a portion of the target DNA. The second DNA fragment is produced by "shifting" the target DNA. Shifting is effected by any means in which one or both strands of the target DNA are effectively shortened or lengthened or by which such information may be generated.

The sequence of a and b is determinable by comparing $g_0$ and $g_1$, which identify each position on the sequenced duplex. Since the shifted DNA includes all or a portion of the target DNA, the positions of the bases in the target and shifted DNA are related in an identifiable manner, and since some of the bases in $g_0$ and $g_1$ are identical, it is possible to uniquely identify all or a portion of the sequences of both strands of the target DNA.

In particular, both strands of the target DNA, which is double-stranded DNA that may be in closed circular, supercoiled, or linear form, are simultaneously sequenced after denaturation by chemical or physical methods using any method known to those of skill in the art that yields data from which pairs of alternative bases for each position on a single strand may be generated. The Sanger dideoxy chain termination method is preferred herein.

The sequencing methods described herein provide a means to unravel the sequence of at least one of the strands by sequencing a second DNA fragment that is "shifted" by a known amount with respect to the first. Comparison of the shifted and unshifted data pairs makes it possible to completely determine the sequence of the DNA fragment. In fact, in certain preferred embodiments, the information is sufficiently redundant to accurately determine the complete DNA sequence of both strands and to permit error detection and, in certain circumstances, correction.

In preferred embodiments, it is possible to determine a DNA sequence by sequencing both strands of a double strand in two four-lane gels. Computer simulation analyses (see, e.g., Example 6), which assume that the shifted DNA includes all of the target DNA, indicate that the total number of sequencing events, including chain syntheses and gel separations, needed to achieve a desired level of accuracy can be reduced by up to a factor of two using the double-stranded technique.

In addition, in embodiments in which the shifted DNA includes a substantial portion (more than at least about 50%) of the target DNA, this method provides a means to detect errors, and, in certain embodiments, correct errors. The presence of complementary strand data permits error detection and in some circumstances error correction.

Both the Maxam Gilbert and Sanger methods rely on reactions that sequence both strands of DNA from one end. Consequently, if both strands are sequenced simultaneously, strand a and its complement b are both sequenced from their 5' ends, the resulting sequence information includes data pairs that represent alternative bases for a location on one or the other strand.

For example, a target DNA fragment that has the sequence:

a 5' AATGCG 3' a' 3' TTACGC 5', would, upon sequencing, generate pairs of alternative bases as follows: {AC}, {AG}, {CT}, {AG}, {CT}, and {GT}, which data set is herein referred to as gel data $g_0$. The first pair of bases are the alternative bases for each of the 5' ends of the strands, the second pair are the alternative bases for the second from the 5' end of each strand, and so on. Without more information, it is impossible to uniquely assign each base in each pair to one strand or the other. If, however, it was known that the first base on the 5' end of strand a is an A, then, because the last base on the 3' of strand a must be a T, the last base on the 5' end of strand a must be a G. Further, because of the complementarity of the strands, the base at the 5' end of strand a' must be C. Thus, knowing the identity of one base permits a portion of the other bases in the duplex to be unambiguously identified. If more information about the strands were available, it would be possible to unravel all or part of the sequence of both strands.

In a preferred embodiment, the target DNA is shifted by the addition of one or more known bases to one strand. Both strands of the target DNA are simultaneously sequenced yielding gel data $g_0$. The shifted double-stranded DNA molecule is also sequenced to produce a second set of gel data $g_1$. The data $g_0$ is compared to the data $g_1$. Since at least one base is known, one can sequentially determine both bases using the analysis presented herein. When the positions of the bases cannot be unambiguously deduced, either the shifted DNA did not include sufficient sequence in common with the target DNA or a sequencing error occurred. In embodiments in which the entire sequence of the target DNA is included in the shifted DNA, many errors can be corrected. The inability to unambiguously deduce a particular base, however, indicates that a more subtle error has occurred. To unambiguously correct such an error, the target DNA is shifted by a different amount and the second shifted DNA is sequenced to produce data set $g_2$. The correct sequence may be obtained by comparing $g_0$ and $g_2$, or $g_1$ and $g_2$.

The amount of information, and, thus, ability to detect and correct errors, is a function of the selected shift. In instances in which the entire sequence of the target DNA is included in the shifted DNA, sufficient information is provided to completely sequence both strands of the target DNA, to detect errors and, in preferred embodiments, particularly those in which the target DNA is about 300 base pairs or less, to correct most errors.

Information Content

The amount of information provided by the disclosed methods can be quantified by calculating the entropy from information theory (see e.g., Abramson (1963) *Information Theory and Coding*, McGraw-Hill, N.Y.). In acordance with the methods herein, the information content duplex sequencing event is as great as more than 50% higher than that obtained using conventional single-stranded sequencing. In practice, therefore, the methods herein provide means for sequencing that require fewer reactions and gel separations in order to achieve a desired level of accuracy.

The above considerations on the amount of information held in the various sequencing techniques can be quantified by introducing the information content function (Abramson (1963) *Information Theory and Coding*, McGraw-Hill, N.Y.):

$$H = - \sum_{i=1}^{N} p_i \log p_i,$$

where $p_i$ is the probability of a certain reading at one location on the gel and N is the number of possible different types of readings at that location. Assuming that a single-strand has a random distribution of bases, then the data at one location is one of the four possibilities, (A,C,G, or T), and the probability for each is ¼. The resulting H for a single strand is therefore 1.39. This H is actually the information/location so that the total information is H times the number of bases in the strand.

For a double strand the data at one gel location is one of ten possibilities (N=10): ({A}, {C}, {G}, {T}, {A,C}, {A,G}, {A,T}, {C,G}, {C,T}, {G,T}). For two random strands the probability of occurrence for each of the first four is 1/16 while the probability of occurrence for each of the last six is ⅛. This yields a total H of 2.25.

Ignoring strand complementarity for the moment, the double-stranded data provides an information content of 2.25 and the single stranded data provides an information content of 1.39. The double-stranded sequencing data must be augmented by a second sequencing with a shift to obtain the full sequence data. When there are errors, the additional information provided by the required two sequencings can be used for error detection and correction. The information content from two double-stranded sequencings is 4.5, while the information content from two single-stranded sequencings, three single-stranded sequencings, and four single-stranded sequencings is 2.78, 4.17 and 5.56, respectively. This indicates that the error correcting capabilities of the method herein, is between that of three and four single-stranded sequencings.

The information content may be understood from a related point of view by noting that since there are four bases, a single base can be represented by two binary digits or two bits, i.e., $\log_2 4 = 2$. The double-stranded gel readings are encompassed by the ten different possibilities given above and thus the number of "bits" required to represent one reading is $\log_2 10 = 3.32$. The ratio of required bits is $3.32/2 = 1.66$, while the ratio of entropies is $2.25/1.39 = 1.62$. These do not agree exactly because, for random strands, the probability of occurrence of the ten readings are not all equal.

Thus, two sequencing events in which both strands of the target DNA are simultaneously sequenced and both strands of the shifted DNA, which includes all or a portion of the target DNA, are simultaneously sequenced, can provide sufficient information to correctly sequence the DNA fragment and, in certain embodiments, permits detection of sequencing errors. Furthermore, correction of errors generated in the sequencing process, can be effected by introducing a second shift of a different known number of bases and sequencing this DNA. The information from that sequencing event is compared with either the unshifted data or the first shifted data and the error is corrected.

Preparation of shifted DNA

Use of shifted DNA is the core of the methods described herein. In order to practice the methods herein, shifted DNA, in which one or more known bases is added to or deleted from one or both strands of the target DNA must be prepared. Shifting may be effected by any method known to those of skill in the art by which target DNA is modified such that the one or both strands of the resulting DNA is of a different length than the target DNA. In addition, the target DNA may also be modified. It is only necessary that the so-called target DNA and the shifted DNA are different in that the shifted DNA differs from the target DNA by the addition or deletion of one or more bases from one or both strands.

(1) Preparation of shifted DNA in which only one strand is shifted

In preferred embodiments, shifting is effected by any method that renders one of the strands of the target DNA longer than the other strand. This may be effected by adding or removing unequal numbers of bases to or from the complementary strands of the target DNA and may be accomplished by any method known in the art. For example, if sufficient information is available to construct primers for sequencing, the shift can be introduced by modifying the length of one of the primers for initiating sequencing of each of the strands of the double-stranded DNA. Primers of different lengths are only used to sequence the shifted double-stranded DNA molecule to generate the $g_1$ gel data. Primers of identical length may also be added to the target DNA and used to sequence the unshifted double-stranded DNA to generate the $g_0$ gel data.

For example, primers of unequal length can be produced by synthesizing primers complementary to sequences adjacent to the 5' ends of each complementary strand of the target DNA. Such sequences may originate from different strand-specific restriction sites in a vector into which the target DNA has been cloned. Denaturation renders these regions available for annealing with the synthetic primers of different lengths.

In preferred embodiments, the target DNA may be cloned into plasmid vectors that contain dual oppositely oriented promoters or other sites of known sequence. If necessary, the DNA may be amplified by replicating the plasmids. Following denaturation, oligonucleotides of different lengths, complementary to the promoters or other such sequence, are used to prime the chain termination sequencing reaction of the target DNA inserted between the promoters. The resulting data set is a shifted DNA data set that includes the entire target DNA shifted by different, but known amounts and known sequences, in each strand. Comparison of this data set with the data set produced by sequencing the target DNA, or sequencing the target with primers that differ from at least one of those used to produce the shifted data set, provides a means for completely determining the sequence of the target DNA and detecting and possibly correcting errors.

In most preferred embodiments, the target DNA may be cloned into such plasmid vectors between sites of known sequence, such as oppositely oriented promoters, and, if necessary, amplified by replication in the vector. After amplification and denaturation, one pair of primers complementary to the promoter or other known region on each side of the target DNA may be used to obtain the first data set of alternate base pairs. A second pair of primers, in which at least one differs in length from at least one of the first set of primers and the other primer in the second pair, may be used to generate a second data set of alternative base pairs. Comparison of both data sets permits the entire sequence of the target DNA to be determined, errors to be detected, and depending upon the nature of the shift and location of the errors, errors to be corrected.

The plasmid vectors useful for such embodiments, include, but are not limited to, the twin promoter pGEM ™ plasmid vectors (Mierendorf et al. (1987) *Meth. Enzy.* 152: 556–562), λgt11, and any other such plasmid that may be constructed or purchased. The pGEM ™ plasmid vectors contain the bacteriophage SP6 and T7 RNA polymerase promoters in opposite orientations as specific priming sites for sequencing inserted DNA. The SP6 promoter is a 19-mer and the T7 promoter is a 20-mer. A shifted data set can then be generated by sequencing the DNA inserted into the plasmid using primers complementary to each of the oppositely oriented promoters. The other data set could be generated by priming the reactions with one primer used for the first sequencing and a second primer that is longer or shorter than the second primer used in the first sequencing. Alternatively, both primers could be of different lengths than those used in the first sequencing.

The cloning vector λgt11 may also be used for generating shifted sequences. Primers of different lengths that are complementary to the lac Z sequences adjacent to the EcoRI site may be used (see, e.g., Mehra et al. (1986) *Proc. Natl. Acad. Sci., USA* 83: 7013–7017) to generate data sets of alternative base pairs.

Shifted DNA in which one strand is longer or shorter than the other strand may also be prepared by first amplifying the DNA by adding tails of known sequence as described below (see, also, FIG. 5) and simultaneously sequencing both strands of the tailed DNA using primers complementary to the tails. The sequence information obtained from sequencing this DNA may be used to prepare and sequence shifted DNA by using primers that differ in length. For example, if the primer complementary to the tail is represented by NNNN and the data pair from the first sequencing event for the first nucleotide beyond the primer is {T,C}, then, by using and constructing and using primers NNNA and NNNNG, the resulting sequence data will be shifted in one strand by one known base because each primer is of a different length and is unique to one strand.

Any other method known to those of skill in the art that results in DNA that is shifted in at least one strand compared to the target DNA or that generates a shifted data set of alternative bases may be used.

(2) Preparation of shifted DNA in which both strands are shifted (a) Restriction digests to produce shifted fragments The target DNA may be cut with a restriction enzyme that preferably cuts at one site to produces two distinguishable fragments. Comparison of the data set generated by simultaneously sequencing both strands of the target DNA with that generated by sequencing one of the restriction fragments permits all or a portion of the sequence of the target DNA to be deduced. If the sequenced restriction fragment includes more than half of the target DNA, the entire sequence of the target DNA may be deduced. If more than one of the restriction fragments and the target DNA are sequenced, the entire sequence of the target DNA may be deduced and errors may be detected. If all of the restriction fragments and the target DNA are sequenced, the entire sequence of the target DNA can be deduced, errors can be detected and corrected. In preferred embodiments, a restriction enzyme is selected that cleaves at a single site in the target DNA to produce two fragments of unequal length. Simultaneously sequencing both strands of the target DNA and simultaneously sequencing both strands of the longer restriction fragment permits the entire sequence of the target DNA to be deduced. If both restriction fragments are sequenced, errors may be detected and corrected.

Restriction mapping may also be combined with the sequencing method. A map of a long sequence of DNA can be constructed by first cutting it into smaller pieces using a restriction enzyme to produce a set of fragments $f_1$; the same long sequence can also be cut into a different set of fragments, $f_2$, using a different restriction enzyme. A double-stranded sequencing of all of the fragments should provide enough information to reconstruct the initial long strand. In effect, the use of the second restriction enzyme provides both the shift necessary for sequencing the fragments and the overlap information necessary to order the fragments. The algorithm required to determine the sequence is more complicated in this case because the extent of the shift is a priori unknown. If the initial fragments are still too large for sequencing, this process could repeated with enzymes that cut more frequently. Because of error-correcting properties of the double-stranded sequencing technique, it should be necessary to sequence fewer overlapping fragments to obtain the complete sequence than when using single-stranded sequencing methods.

(b) Generation of nested deletion mutants to produce shifted DNA

Methods using enzymes, such as BAL 31, exonuclease III, and pancreatic DNAase, that are designed for the preparation of nested inserts of deletion mutants that lack progressively more nucleotides from one end or the other of the target DNA (see, e.g., Sambrook et. al. (1989) *Molecular Cloning: A Laboratory Manual*, 2nd Ed., Cold Spring Harbor Laboratory Cold Spring Harbor, N.Y., at p. 13.34–13.44) may be used to generate shifted DNA. Each deletion mutant is shifted with respect to the target DNA. Simultaneous sequencing of both strands of one or more of the deletion mutants and of both strands of the target DNA, permits all or a portion of the sequence of the target DNA to be unraveled.

Sequencing methods for the generation of the data sets of alternative base pairs Any sequencing method known to those of skill in this art which can be used to simultaneously sequence both strands of a duplex DNA fragment and which generates data sets of alternative base pairs as defined herein may be used. In preferred embodiments the Sanger chain termination method is used to obtain the requisite data sets.

(1) Selection of and preparation of the double-stranded template DNA for sequencing Isolated double-stranded DNA in circular, nicked circular, and linear form are all appropriate templates. If necessary, the quality of the template for sequencing may be improved by methods known to those of skill in the art, such as alkaline denaturation of DNA combined with hydrolysis of RNA (Hsiao (1991) *Nucl. Acids Res.* 19: No. 10,2787), and the use of gene 32 binding protein (Kaspar et al. (1989) *Nucl. Acids Res.* 17: 3616), and the use of detergents to prevent reannealing of primers (Bachmann et al. (1990) *Nucl. Acids Res.* 18: 1309).

(2) Selection of and preparation of primers for DNA sequencing

The Sanger method and amplification methods require primers for initiation of second strand synthesis. If the sequences of the terminal regions is unknown, primers may be provided in a number of ways. For example, universal primers are designed to anneal to vector sequences adjacent to cloned target DNA fragments. Universal primers are typically 15–29 nucleotides in length and anneal to sequences immediately adjacent to restriction sites, such as the HindIII site in the polycloning region of bacteriophage M13mp18, and the EcoRI in the polycloning region of the bacteriophage M13mp19 (Sambrook et al. (1989) *Molecular Cloning: A Laboratory Manual*, 2nd Ed., Co;d Spring Harbor Laboratory Cold Spring Harbor, N.Y., at p. 13.6). In addition, primers complementary to restriction endonuclease recognition sequences, may be used. Such primers are particularly useful if the target DNA has been cloned into vectors at the given restriction sites in order to reproduce the DNA segment before sequencing.

These restriction sites then provide the sequences for synthetic primers initiating the sequencing reaction.

In addition, the amplification method herein uses palindromic primers. Such palindromic primers may be selected or designed to include convenient restriction endonuclease sites. Thus, primers complementary to added homopolymeric or palindromic tailings at the 3' end of each strand may be used. Palindromic or homopolymeric primers anneal with the added tail and prime the DNA synthesis reaction both in the sequencing or amplification reactions. Other primers include those complementary to the commercially available twin promoter vectors, such as the pGEM TM plasmids and other such plasmids (see, e.g., Mierendorf et al. ((1987) *Meth. Enzy.* 152: 556–562; and Mehra et al. (1986) *Proc. Natl. Acad. Sci., USA* 83: 7013–7017).

In general, synthetic primers which anneal to one or both of the complementary strands may be of any length, preferably about 15-mers and longer, as long as they of sufficient length to uniquely prime DNA synthesis from the selected site or sites. The selected primer or primers is a function of the target and shifted DNA. For example, if the target DNA has been cloned into a particular vector, preferred primers include those complementary to regions in the vector that flank the inserted target DNA.

(3) Selection of and preparation of DNA polymerase for sequencing

Any DNA polymerase which may be used for DNA synthesis, such as those routinely used for chain termination sequencing and PCR, may be used. These include the Klenow fragment of *E. coli* DNA polymerase I, reverse transcriptase, and T7 DNA polymerase that have been modified to eliminate the 3' to 5' exonuclease activity. These T7 DNA polymerase are called SEQUENASE TM and SEQUENASE TM version 2.0 TM (Tabor et al. (1987) *Proc. Natl. Acad. Sci.* 84: 4767.) Thermostable Taq DNA polymerase, isolated from *Thermus aquaticus*, which is efficient at 70°–75° C., a temperature that precludes the formation of secondary structures even in templates that are rich in G and C may also be used.

Amplification of the target and shifted DNA

Sufficient quantities of DNA may be produced for sequencing by any method known to those of skill in the art. The DNA fragment of interest may cut into appropriate sizes, approximately 400–800 base pair or shorter lengths, and cloned in an appropriate vector and replicated in a host cell, such as *E. coli*. The restriction sites at which the target DNA is cloned into the vector provide known sequences from which primers that will anneal to these sites can be synthesized.

The DNA can also be amplified using the polymerase chain reaction (PCR) (U.S. Pat. No. 4,683,202 to Mullis et al.). PCR relies on the use of oligonucleotide primers that are complementary to the 3' ends of the DNA of interest. Selection or synthesis of primers requires sequence information on both sides of the DNA of interest. When the DNA of interest has yet to be sequenced such information is unavailable. It is, thus, necessary to obtain such information or to devise means that avoid the need for obtaining such information.

For example, the DNA fragment of interest may be cut with restriction enzymes to provide DNA fragments that terminate with a known sequence of sufficient size to form a unique priming site or to introduce the DNA into a restriction site in a plasmid or other DNA molecule, such that, upon, restriction with the same or a second restriction enzyme, DNA fragments with known 3' ends are generated.

In preferred embodiments herein, the target DNA may be amplified by the method provided herein in which tails of known sequence are added to both ends of the DNA fragment. This method provides a means for amplifying the target DNA for which no sequence information is available and also provides a means for generating shifted DNA.

In practicing this method, double-stranded tails of known sequence are added to the 3' termini of each strand so that upon addition of the primer complementary to the known sequence, PCR can be effected or both strands may be simultaneously sequenced. Because there is no way to control the orientation in which the oligonucleotide tail is ligated, addition of any tail to both ends cannot, however, be accomplished, merely by blunt end ligating any oligonucleotide to the ends of the target DNA. This problem has been solved herein by selecting the tails in a manner such that either orientation is identical. For example, this can be accomplished by blunt end ligation of palindromic tails to the target DNA or by enzymatic addition of homopolymer tails or by attaching any tail for which the tail is identical whether it is added to the 5' or 3' terminus.

Thus, a homopolymer tail for use as a complementary sequence for primer extension may be added by treating a double-stranded DNA fragment with terminal transferase, which, under appropriate conditions, acts on single stranded DNA with a 3' OH terminal or double stranded DNA with a protruding 3' OH, and a single deoxyribonucleotide, such as dTTP, to form a single-stranded homopolymer tail at the 3' end of each strand of the double-stranded DNA. Blunt-ended double-stranded DNA or DNA with recessed 3' OH can serve as a template for terminal transferase when $Co^{+++}$ is used as a cofactor. Complementary tails such as poly dA, of a selected size are annealed to the homopolymer single strands and ligated to the 5' ends of each strand of target DNA. If necessary, excess single strands may be removed from the resulting DNA by digestion with an appropriate enzyme, such as $S_1$ nuclease. An oligonucleotide, such as the poly dA used for forming the double-stranded DNA, may also be used as a primer for subsequent PCR amplification of the DNA or subsequent simultaneous sequencing of both strands of the DNA.

In an alternative embodiment, double-stranded palindromic sequences may be added to the target DNA by blunt end ligation. Preferred palindromic sequences are selected so that upon renaturation of the DNA, target DNA anneals to target DNA. Such palindromic primers may also include restriction endonuclease sites for convenient manipulation of the amplified DNA. The palindromic tails must be sufficiently long to serve as primers, but not too long so that they substantially interfere with target DNA renaturation of lead to the formation of concatomers. Accordingly, the preferred palindromic sequence will generally be AT-rich. The palindromic sequence may be linked to the target DNA by any method known to those of skill in the art. For example, the target DNA is first blunt ended with S-1 exonuclease, which selectively digests single-stranded DNA. When the strands are separated the palindromic tails on the 3' termini provide sequences to which free palindromic oligomers may anneal to form primers for the PCR reaction. Alternatively, single palindromic sequences are attached at the 3' termini of each complementary strand, providing sequences for annealing of the primers. Free oligomers anneal to these sequences, acting as primers from the 5' termini so that amplification may proceed.

When palindromic primers are used, any subsequent PCR reaction may be modified by the addition of ligase under conditions whereby complete second strands are formed (see FIG. 5).

This amplification method may be used to generate shifted DNA because the resulting DNA includes the added tails and, thus, differs in length from the target DNA. Since the sequence of the added tail is known, sequencing both strands of the amplified and target DNA permits the entire sequence of the target DNA to be determined.

Analysis of the sequencing data (1) Analysis of the sequencing data produced when the shifted DNA is produced by altering the length of one strand of the DNA compared to the other strand.

Two complementary single strands are considered, a and b, whose sequence of bases are given by $$a = \{a_1, a_2, \ldots, a_n\} \quad (1)$$

$$b = \{b_1, b_2, \ldots, b_n\} \quad (2)$$

in which $a_i$ and $b_i$ are the ith base of sequences a and b respectively, and $1 \leq i \leq n$ and each of the bases is A, C, G, T.

The double strand gel data, $g_0$, contains a set of unordered pairs, $\{a_i, b_i\} = \{b_i, a_i\}$, that is, $$g_0 = \{\{a_1, b_1\}, \{a_2, b_2\}, \ldots \{a_n, b_n\}\}, \quad (3)$$

where $g_{0i}$ denotes the ith element of $g_0$, $\{a_i, b_i\}$.

Considering the case in which the shifted DNA is produced by addition of a single nucleotide $b_0$ to one end of the target, the shifted gel data set, $g_1$, is:

$$g_1 = \{\{a_1, b_0\}, \{a_2, b_1\}, \ldots, \{a_n, b_{n-1}\}, \{b_n\}\} \quad (4)$$

Given only the gel sequences $g_0$ and $g_1$, and assuming that $b_0$ is known, the sequences of a and b can be completely determined as follows.

Starting from the 3' end of the strands (i.e. the data obtained from the top of the gel, if the chain termination method of sequencing is used), (this is herein referred to as the "top down" algorithm):

$$b_0 = \text{known} \quad (5)$$

$$a_i = f(b_{i-1}, g_{1i})$$

$$b_i = f(a_i, g_{0i}),$$

where $$f(x, \{y, z\}) = \begin{cases} z & x = y \\ y & x = z \\ \emptyset & x \text{ is} \neq y \text{ and } x \neq z \end{cases} \quad (6)$$

and $\emptyset$ denotes the null answer, meaning that an error has occurred and the next base cannot be determined. Similarly, considering the data pairs from the 5' to 3' end (herein referred to as the "bottom-up" algorithm):

$$b_n = \text{known}$$

$$a_i = f(b_i, g_{0i}) \quad (7)$$

$$b_{i-1} = f(a_i, g_{1i})$$

By combining the top-down and bottom-up algorithms, each of the positions in strand a and the complementary strand b may be determined. When the algorithms cannot be solved, there has been at least one error made in the sequencing process.

In order to correct an error which has been detected, but cannot be corrected, in the comparison of $g_0$ and $g_1$, a second shift can be performed using a different number of known bases. If, for example, the second shift is two known bases, the gel data from sequencing the second shifted double-stranded DNA is:

$$g_2 = \{\{a_1, b_{-1}\}, \{a_2, b_0\}, \ldots \{a_2, b_{n-2}\}, \{b_{n-1}\}, \{b_n\}\} \quad (8)$$

The sequences of a and b can be deduced by any combination of two data sets, that is, $g_0$ and $g_1$, or $g_0$ and $g_2$, or $g_1$ and $g_2$, will produce the a and b sequences. If the $g_0$ and $g_1$ comparison produces a null answer, which indicates an indicates an error, then $g_0$ and $g_2$ or $g_1$ and $g_2$ would indicate the correct sequence.

(2) Generalized analysis of the data that assumes no a priori known bases and any type of shift The unshifted data set is given by $$g_0 = \{\{a_1, b_1\}, \{a_2, b_2\}, \ldots \{a_n, b_n\}\}, \quad (3)$$

and the shifted data is obtained by shifting the a strand by i bases and the b strand by k bases $$g_1 = \{\{a_{i+1}, b_{k+1}\}, \ldots \{a_{i+m}, b_{k+m}\}\}. \quad (9)$$

The initial strands are of length n and the sequenced shifted strands are of length m.

The slightly more general case where the strand length of a and b sequenced in $g_1$ are unequal may be readily extended from the following analysis. Since a and b are complementary strands means, then $$b^-_{n+1-i} = a_i$$

and $$b_{n+1-i} = a^-_i.$$

Therefore $$g_0 = \{\{a_1, a^-_n\}, \ldots \{a_n, a^-_1\}\}$$

or $$g_{0j} = \{a_j, a^-_{n+1-j}\} \quad (10)$$

and $$g_1 = \{\{a_{i+1}, a^-_{n-k}\}, \ldots \{a_{i+m}, a^-_{n-k-m+1}\}\} \quad (11)$$

or $$g_{1j} = \{a_{i+j}, a^-_{n+1-k-j}\} \quad (12)$$

The sequence is determined by first considering what information is available for $a_j$ with j taking the values from 1 to n. Two readings of $g_0$ contain information on $a_j$ and they are redundant. They are $$g_{0j} = \{a_j, a^-_{n+1-j}\} \quad (10)$$

and $$g^-_{0n+1-j} = \{a^-_{n+1-j}, a_j\} \quad (12)$$

The redundancy is useful for error detection and correction but in general the information from $g_{0j}$ only narrows the choice for $a_j$ between two bases but does not determine it.

Turning to the information contained in $g_1$, if $i+1 \leq j \leq i+m$, then $$g_{1j-i} = \{a_j, a^-_{n+1-k-j+i}\} \quad (13)$$

Furthermore, if $n-k \geq j \geq n-m-k+1$, then $$g^-_{1n+1-k-j} = \{a^-_{n+1-k-j+i}, a_j\} \quad (14)$$

As in the case of $g_0$ data, the two $g_1$ readings are redundant. If, however, $k \neq i$, then, in general, $a_{n+1-j} \neq a_{n+1-j-(k-i)}$, and $a_j$ is determined by comparing the $g_0$ and $g_1$ data. If $a_{n+1-j} = a_{n+1-j-(k-i)}$, the analysis continues by next examining the four readings containing $a_{n+1-j}$ information ($g_{0j}, g_{0n+1-j}, g_{1n+1-j-i}, g_{1j-k}$) or four readings containing $a_{n+1-j-(k-i)}$ information ($g_{0n+1-j-(k-i)}, g_{0j+(k-i)}, g_{1j-i}, g_{1n+1-k-j}$). By processing in this manner, all ambiguities can be resolved and the sequence determined.

The requirement $k \neq i$ indicates that, in order to generate new information, the shift of the two strands should be unequal. The inequalities necessary for $g_1$ data to exist, $i+1 \leq j \leq i+m$ and $n-k \geq j \geq n-m-k+1$, indicate that the most information is preserved if $i$ and $k$ are negative, i.e., bases are added and if $m \geq n-k$ and $m \geq n-i$, i.e., no bases deleted. In this instance, two $g_1$ readings exist for all $a_j$. Note that if $i \geq s$ and $k \geq s$, no $g_1$ readings exist for $a_j$, $j \leq s$.

Error analysis and sequence correction

(1) The role of complementarity in error analysis and sequence correction

For two unrelated strands, which are not complementary, if a single error occurs in gel data $g_0$ or $g_1$: (1) it is detectable but not correctable, (2) the minimum number of undetermined bases is one, and (3) a larger number of undetermined bases can arise only if both gel sequences contain only two bases in the identified range where the error occurs. Virtually all errors of this type can be corrected if the two strands are complementary. To insure correction of all single errors by complementarity, a strand must be an even number of bases in length and the shifted sequence must be shifted by an even number of bases.

When two errors occur on a set of gel data ($g_0$ and $g_1$) for two unrelated strands, there are two separate cases to consider. The first case is when the errors are far enough apart that they can be separately identified. The analysis for this case is essentially identical to that for single errors. The second possibility arises when the errors are sufficiently close to each other that the two errors "may cancel each other out" and thereby go undetected. For this second case, the complementarity of the strands provides a means to detect errors, but because there is no way to determine whether the strand data or the complementary data is correct, does not determine any way to correct the error. To resolve which bases are correct in situations such as this, an additional, double-stranded sequencing may be performed with a shift of a different number of bases.

The above analysis is specific for the case in which the shifted DNA is produced by shifting one strand of the target DNA by a known number of bases. This analysis may be modified in order to deduce the sequence of target DNA in which the shifted DNA is produced by altering the length of both strands and or in instances when the known base occurs at a site other than the terminus of a strand. In such instances, when the shifted DNA contains less then the entire target DNA, it may not be possible to detect errors.

This analysis is described in greater detail in Examples 3, 4 and 5. The relative frequency of occurrence of the above errors and how well double-stranded sequencing compares with single-stranded sequencing is described in the Example 6, via computer simulation.

(2) Detection and correction of errors

In practice, errors arise when a base is not detected or its identity not resolved. In particular, when the Sanger method is used for sequencing, many errors arise from an undetected or missing base and from reading a poorly resolved gel. Because the single strands a and b are not independent, but are complementary, additional information for error detection and correction is available when practicing the sequencing methods herein.

One error that occurs when the chain terminator sequencing technique is used, arises because not enough chains of a given length are produced to be detected. This results in a missing base, unless the correct gel reading for a given length has identical alternative bases, such as $\{A,A\}$. On the other hand, a correct gel reading of $\{A,C\}$ will be read as $\{A,A\}$ or $\{C,C\}$ if one of the bases is missing.

Another error which could occur from reading a poorly resolved gel is an "interchange" or "inversion" error. That is, $g^*_{0j} = \{a_{j+1}, b_{j+1}\}$ and $g^*_{0j+1} = \{a_j, b_j\}$. Starting with the top-down algorithm, $g_{0j}$ is encountered while determining $b_j$:

$$b^*_j = f(a_j, \{a_{j+1}, b_{j+1}\}) = \begin{cases} b_{j+1} & a_j = a_{j+1} \\ a_{j+1} & a_j = b_{j+1} \\ \emptyset & a_j \neq \{a_{j+1}, b_{j+1}\} \end{cases} \quad (15)$$

In order for the error to not be detected, $a_j = a_{j+1}$ or $a_j = b_{j+1}$. Considering $a_j = a_{j+1}$, then $b^*_j = b_{j+1}$ and $$a^*_{j+1} = f(b^*_j, \{a_{j+1}, b_j\}) = \begin{cases} a_{j+1} & b_{j+1} = b_j \\ b_j & b_{j+1} = a_{j+1} \\ \emptyset & b_{j+1} \neq \{a_{j+1}, b_j\} \end{cases} \quad (16)$$

Again a choice between $b_{j+1} = b_j$ and $b_{j+1} = a_{j+1}$ must be made. Since, however, the inversion error occurs if $a_j = a_{j+1}$, the choice $b_{j+1} = b_j$ is a trivial one because then $g_{0j} = g_{0j+1}$. Therefore, $b_{j+1} = a_{j+1}$ which implies $a^*_{j+1} = b_j$. The next base is then given by $$b^*_{j+1} = f(a^*_{j+1}, \{a_j, b_j\}) = f(b_j, \{a_j, b_j\}) = a_j = a_{j+1} = b_{j+1}, \quad (17)$$

which is the correct value. Therefore the inversion $g^*_{0j}=\{a_{j+1},b_{j+1}\}$ and $g^*_{0j+1}=\{a_j,b_j\}$ with $a_j=a_{j+1}=b_{j+1}$ is undetectable. Furthermore it is a special example of the double errors discussed above and in the Examples, since with $a_j=a_{j+1}$ the a's are unchanged.

Returning to Equation (15) and assuming $a_j=b_{j+1}$. Then $b^*_j=a_{j+1}$ and $$a^*_{j+1}=f(b^*_j, \{a_{j+1}, b_j\})=f(a_{j+1}, \{a_{j+1}, b_j\})=b_j \quad (18)$$

and $$b^*_{j+1}=f(a^*_{j+1}, \{a_j, b_j\})=f(b_j, \{a_j, b_j\})=a_j=b_{j+1}, \quad (19)$$

which is also correct. This case is less restrictive than the previous, requiring only $g^*_{0j}=\{a_{j+1}, b_{j+1}\}$ and $g^*_{0j+1}=\{a_j,b_j\}$ with $a_j=b_{j+1}$. This can also be viewed as an example of a double error with $b_j \to a_{j+1}$ in $g_{0j}$ and $a_{j+1} \to b_j$ in $g_{0j+1}$.

An inversion error is readily detected if a shift of more than one base is used, because the two errors occur in different subsequences. See, e.g., Example 4.

(2) Error detection when complementary strands are sequenced since target DNA is duplex DNA, the two single strands a and b are not independent but are complementary to each other. Complementarity provides additional information that can be used for error detection and correction.

As discussed above, when a single error occurs, the region in which it occurs cna be identified. In the simplest case there is an unresolved base at only one location of one stand, $a_i$. If the two strands are complementary, then $b^-_{n-i+1}=a_i$ where the superscript $-$ indicates complement and n is the total length of the strand. In this case $b^-_{n-i+1}$ can be used to assign the correct value to $a_i$.

In order to insure that single errors are corrected, a strand must be even in length and the shifted sequence must be shifted by an even number of bases. This can be understood by considering the following. If the length of the strand is an odd number of bases, a problem can occur for $i=n-i+1$, i.e., $i=(n+1)/2$, which is the midpoint of the strand. That is $b^-_{n-i+1}=a_i$ becomes $b^-_{(n+1)/2}=a_{(n+1)/2}$ and if both values are undetermined due to a single error, complementarity cannot correct the error. Therefore, in order to insure correction n must be an even number.

Alternatively, if instead of shifting by one base the DNA is shifted by k bases:

$$g_{ki}=\{\{a_1,b_{1-k}\},\{a_2,b_{2-k}\},\ldots,\{a_j,b_{j-k}\},\ldots,\{b_{n+1-k}\},\ldots,\{b_n\}\},$$

then, by analogy with Equations (5-7), the k subsequences are determined independently of each other. Thus, $\{a_1, a_{1+k}, a_{1+2k}, \ldots, a_{1+rk}\}$ and $\{b_1, b_{1+k}, b_{1+2k}, \ldots, b_{1+rk}\}$, in which r is an integer, are determined independently from the other bases, as are $\{a_2, a_{2+k}, a_{2+2k}, \ldots, a_{2+rk}\}$ and $\{b_2, b_{2+k}, b_{2+2k}, \ldots, b_{2+rk}\}$, and so on. Consequently an error in subsequence 1 does not propagate to any of the other sequences. In order to insure that any single error is correctable by complementarity, it is only necessary that a second error does not occur in the complement of a base in the same sequence as the base. The complement of $a_i$ is $b^-_{n-i+1}$. If these appeared in the same sequence, then $i=q+p_1k$, where q is an integer between 0 and $k-1$ and determines the subsequence, while $p_1=1,2,3,\ldots$ determines the element of that subsequence.

The index of the complement, $n-i+1$, becomes $n-(q+p_1k)+1$. If this can be written in the form $q+p_2k$, the complement of a is in the same subsequence as a and $n-q-p_1k+1=q+p_2k$, or $n+1=2q+(p_2+p_1)k$. Now, if n is an even number and k is chosen to be even, the above relation cannot be satisfied, complementary values occur in different subsequences, and all single errors can be corrected by complementarity.

The undetectable double errors discussed can be detected using complementarity but cannot be corrected because there is no way to determine whether the strand or its complement is the correct one. For the double error case, the issue of complementarity near the middle of the strand is analogous to the single error situation discussed above. To insure that complementarity detects all hidden double errors, it is again necessary to have an even-length strand and to shift by an even number of bases.

The following examples are included for illustrative purposes only and are not intended to limit the scope of the invention.

EXAMPLE 1

Sequencing double-stranded DNA using a single base shift on one strand

The target DNA a 5'-CATTC-3'
b 3'-GTAAG-5'

(S in FIG. 1) is separated and sequenced using the ddNTP chain termination technique to produce the following complementary fragments from a (S): ddGTP produces G and GAATG; ddTTP produces GAAT; ddATP produces GA and GAA, and ddCTP does not produce any radiolabelled fragments (see, FIG. 1). Similarly, the fragments from the complementary strand b (S$^-$) are: ddGTP does not produce any radiolabelled fragments; ddTTP produces CAT and CATT; ddATP produces CA; and ddCTP produces C and CATTC.

The fragments from each of the reactions are run on four lanes of a separating gel, which separates the oligonucleotides by size. The data set representing the possible positions of the bases in each strand is referred to as $g_0$ and is given by:

$$g_0=\{\{C,G\},\{A,A\},\{A,T\},\{T,T\},\{C,G\}\}$$

Since it cannot be determined which base is on the a strand and which is on the b strand, the data from sequencing each strand is insufficient to completely determine the sequence of the target DNA.

Next a base, T, for example, is added to the 3' end of the original strand a to produce a shifted DNA fragment that contains strands $a_1$ and b (S and S in FIG. 1):

$a_1$ 5'-CATTCT-3'
b  3'-GTAAG-5'.

This shifted DNA fragment is denatured and sequenced as above to produce a second set of complementary oligonucleotide fragments, A, AG, AGA, AGAA, AGAAT, and AGAATG from $a_1$ and C, CA, CAT, CATT and CATTC from b. These oligonucleotides are run on a separating gel and the data set obtained is referred to as $g_1$, in which $$g_1=\{\{A,C\},\{A,G\},\{A,T\},\{A,T\},\{C,T\},\{G\}\}.$$

Figure 2:
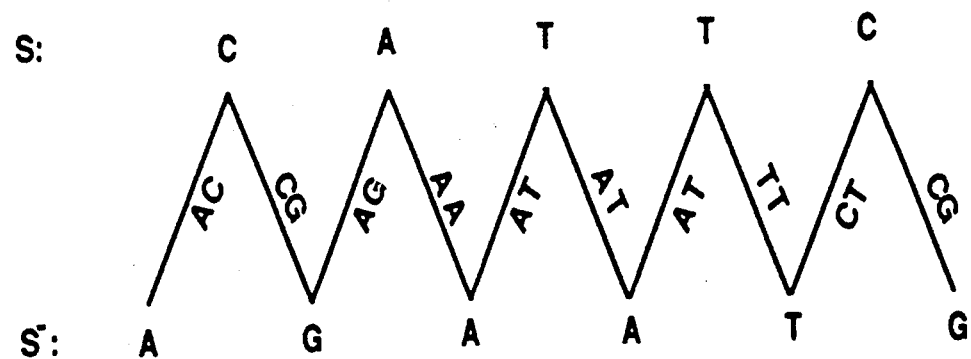
FIG. 2 shows a diagrammatic identification of the complete identification of the strands S and $S^-$ using the data from $g_0$ and $g_1$. The two letter combinations tilted upwards are the components of $g_1$ and those tilted downward are the components of $g_0$. The last element of $g_1$, which is not shown, identifies the last base in strand $S^-$ as G.

Then, $g_0=\{\{C,G\},\{A,A\},\{A,T\},\{T,T\},\{C,G\}\}$ is compared with $g_1$ to assign each base to a strand. Since strand b is common to both data sets and strand $a_1$ is the same as a, except that a single base has been added, comparison of $g_0$ with $g_1$ permits the sequence of the target DNA to be deduced. The comparison is shown in FIG. 2. Since T, which has been added to a to produce $a_1$, is a known base, and both sequenced fragments include an identical strand b, and $g_0$ and $g_1$ are known, the identity and position of all of the bases in the complementary strands may be determined.

This same analysis is used when more than one base is added to one of the complementary strands.

EXAMPLE 2

Sequencing double-stranded DNA using a double base shift in which both strands are shortened in the shifted DNA.

Assuming that the sequence of the target DNA is:

a 5' ACATTCA 3'
b 3' TGTAAGT 5' or
b 5' TGAATGT 3' and the shifted DNA has the sequence:
$a_2$ 5' ACATT 3'
$b_2$ 3' TGTAA 5'
$b_2$ 5' AATGT 3' so that $a=a_2$ shifted by $-2$ bases (i.e., missing two bases at the 3' end) $b=b_2$ shifted by $+2$ bases (i.e., two additional bases at the 5' end) so that:
$g_0$: {{AT} {CG} {AA} {AT} {TT} {CG} {AT}} =data set from a and b
$g_1$: {{AA} {AC} {AT} {GT} {TT}}=data set from $a_2$ and $b_2$.

Since a and $a_2$ are the same at the 5' end and b and $b_2$ are the same at the 3' and the shift is less than half the length of the target DNA, the entire sequence of the target DNA can be deduced by comparing the data sets. Comparing the first base pairs from $g_0$ and $g_1$ indicates that the first base on a must be an A, since the first base on $a_2$ must be the same as the first base on a. Continuing, since a and $a_2$ are the same at the 5' end, the second base must be a C, the third base an A, the fourth base a T and the fifth base a T. The other end of the target DNA can be deduced because $b=b_2$ at the 3' end. Comparison of the data sets from the opposite end indicates that the last base on the 3' end of b must be a T, the second to last must be a G, the third to last must be a T, the fourth to last must be an A and the fifth to last an A. Then, looking at $g_0$:{{AT} {CG} {AA} {AT} {TT} {CG} {AT}} and deleting each of the bases identified as being derived from the 3' end of b, leaves A, C, T, T, A as the sequence of last five bases of a from the 3' end. This is summarized in the following table:

| | a b | | $a_2$ $b_2$ | |
|---|---|---|---|---|
| 5' | A T | 3' 5' | A T | 3' |
| | C G | | C G | |
| | A T | | A T | |
| | T A | | T A | |
| | T A | 3' | T A | 5' |
| | C G | | | |
| 3' | A T | 5' | | |

EXAMPLE 3

Error analysis and sequence correction

Error analysis for complementary strands

Since the two strands of double-stranded DNA are complementary, if the shifted DNA includes more than 50% of the target DNA and there are no sequencing errors in the data, the entire sequence of the target DNA can be deduced. In the instance in which the shift has been introduced by adding a specified number of bases to one strand of the target DNA and the shifted DNA includes the entire target DNA, use of either the bottom-up or top-down algorithm, described above, completely determines the base sequence of the two strands.

To clarify the role that various pieces of information play in error detection and error correction, the effects of one or two errors in the gel data for two unrelated strands have been considered.

A single error

Consider a single error in either $g_0$ or $g_1$. A single error is one that for one value of i, one and only one of the two bases in $g_{0i}$ or $g_{1i}$ is wrong. With this definition there are four single error possibilities in all: $g_{0i}=\{x, b_i\}$ with $x \neq a_i$, $g_{0i}=\{a_i, y\}$ with $y \neq b_i$, $g_{1i}=\{x, b_{i-1}\}$ with $x \neq a_i$, and $g_{1i}=\{a_i, y\}$ with $y \neq b_{i-1}$. For unrelated strands, if a single error occurs: (1) it is detectable but not correctable, (2) the minimum number of undetermined basis is one, and (3) a larger number of undetermined bases can arise only if both gel sequences contain two bases in the identified range where the error occurs.

If there is a single error, $g^*_{0i}=\{x, b_i\}$ with $x \neq a_i$, it can be detected independently by either algorithm when $f=\emptyset$ is encountered. Using the top-down algorithm (Equation (5)), $g_{0i}$ is used to determine $b_i$. Prior to that $a_1, \ldots a_i$ and $b_0, \ldots b_{i-1}$ will have been calculated correctly. From Equation (5) the last correct value is:

$$a_i = f(b_{i-1}, g_{1i}). \qquad (20)$$

The problem arises where:

$$b^*_i = f(a_i, g^*_{0i}) = f(a_i, \{x, b_i\}) = \begin{cases} x & a_i = b_i \\ \emptyset & a_i \neq b_i \end{cases} \qquad (21)$$

which relies on the fact that $x \neq a_i$, and the superscript * indicates an error. It is not always the case, however, that $f=\emptyset$ at the point that an error occurs. For example, if $a_i = b_i$ above, then a value for $b^*_i$ is obtained, albeit an incorrect one.

Considering the bottom-up algorithm for this same single error, $g^*_{0i}=\{x, b_i\}$. Correct values for $a_n, \ldots, a_{i+1}$ and $b_n, \ldots, b_i$ are obtained before using $g_{0i}$ to calculate $a_i$, $$a^*_i = f(b_i, g^*_{0i}) = f(b_i, \{x, b_i\}) = x \qquad (22)$$

This $a^*_i$ does not agree with the top-down derived value of $a_i$, Equation (20), since $x \neq a_i$. The bottom-up algorithm, considered by itself, has not yet detected an error, but can detect one in the calculation of the next base. From Equation (7):

$$b^*_{i-1} = f(a^*_i, g_{1i}) = f(x, \{a_i, b_{i-1}\}) = \begin{pmatrix} a_i & b_{i-1} = x \\ \emptyset & b_{i-1} \neq x \end{pmatrix} \quad (23)$$

If $b_{i-1} \neq x$, the error is identified at this point from $f = \emptyset$. Even if it is not known that $g_{0i}$ is in error, this can be deduced from consideration of the information gained from the top-down and bottom-up algorithms.

It cannot, however be determined which value of $a_i$ (Equation (20) or Equation (22)) is correct because two pieces of information, $g_{0i}$ and $g_{1i}$, have been used by both the top-down and bottom-up algorithms. One of $g_{0i}$ and $g_{1i}$ must be incorrect, but it cannot be ascertained which one it is. If $g_{0i}$ is incorrect, then $a_i$ determined from $g_{1i}$ by the top-down algorithm is correct. If $g_{1i}$ is incorrect, then $g_{1i} = \{x, b_{i-1}\}$, so that $a^*_i$ determined from $g_{0i}$ by the bottom-up algorithm is correct. Equations (5) and (7) show how this ambiguity comes about. The base $a_i$ appears only in two places, once in $g_{01}$ and once in $g_{1i}$. Therefore, if the two values are in disagreement, there is no way to know which is correct. The error, which had been detected by assuming a and b are arbitrary strands can be corrected, since a and b are complementary.

In the above analysis, two conditions, $a_i \neq b_i$ and $b_{i-1} \neq x$, are imposed to arrive at $f = \emptyset$. If, instead, it is assumed that $a_i = b_i$ or $b_{i-1} = x$ or both, the condition $f = \emptyset$ will occur further from the source of the error and multiple elements of a and b determined separately by the top-down algorithm and the bottom-up algorithm will be in disagreement.

This can be illustrated by returning to the top-down analysis above, this time assuming that $a_i = b_i$. From Equation (21) $b^*_i = x$:

$$a^*_{i+1} = f(b^*_i, \{a_{i+1}, b_i\}) = f(x, \{a_{i+1}, a_i\}) = \begin{pmatrix} a_i & a_{i+1} = x \\ \emptyset & a_{i+1} \neq x \end{pmatrix} \quad (24)$$

If $a_{i+1} = x$, then $$b^*_{i+1} = f(a^*_{i+1}, \{a_{i+1}, b_{i+1}\}) = f(a_i, \{x, b_{i+1}\}) = \quad (25)$$

$$\begin{pmatrix} x & b_{i+1} = a_i \\ \emptyset & b_{i+1} \neq a_i \end{pmatrix}.$$

Continuing in this manner, $f = \emptyset$ is eventually reached when one of the following two conditions is satisfied: $a_k \neq a_{k-1} = \ldots a_{i+1} = x$, which will result in $a^*_k = \emptyset$ or when $b_k \neq b_{k-1} = \ldots = b_i = a_i$ which will result in $b^*_k = \emptyset$. Note that $a^*_{k-1} = \ldots = a^*_{i+1} = a_i \neq x$ and $b^*_{k-1} = \ldots = b^*_{i+1} = b^*_i = x \neq b_i$. So all of these values are in conflict with the values obtained from the bottom-up algorithm. The bottom-up algorithm will have the correct answers (not yet having encountered $g_{0i}$), namely, $a_{k-1} = \ldots = a_{i+1} = x$ and $b_{k-1} = \ldots = b_i = a_i$.

This problem can be turned around, if $g_0$ and $g_i$ are known, but not that $g_{0i}$ is in error, and for definiteness, assuming that $a^*_k = \emptyset$, then an error can be identified from $b^*_{i-1} = \emptyset$ using the bottom-up algorithm and $a^*_k = \emptyset$ from the top-bottom algorithm $(k > i)$ because $k-i$ values of a are in disagreement and $k-i$ values of b are in disagreement. When one value was in disagreement, as discussed above, there were two possible corrections. Here there are $2(k-i)$ values in disagreement and there are $2(k-i)+1$ possible corrections. In determining these conflicting values, both algorithms have used $g_{0i}, \ldots g_{0k-1}$ and $g_{1i}, \ldots g_{1k}$, i.e., $2(k-i)+1$ g values in common. Any one of these g values can be altered to give a consistent set of data.

This can be shown by examining the nature of the error, which was created by transforming $a_i$ to x in $g_0$ in the data. The base $a_i$ appears in the data only twice, once in $g_0$ at $g_{0i} = \{a_i, b_i\}$ and once in $g_1$ at $g_{1i} = \{a_i, b_{i-1}\}$. One way to view the error is that there are either too many bases of type x in $g_0$ or there are too many bases of type $a_i$ in $g_1$. In this instance, since $a_i = b_{k-1} = \ldots = b_1$ and $a_{k-1} = \ldots a_{i+1} = x$, the imbalance can be rectified in a number of ways. Any of $a_i, b_{k-1}, \ldots b_i$ can be converted to an x in $g_1$ or any of $a_{k-1}, \ldots a_{i+1}, x$ can be converted to an $a_i$ in $g_0$. This is illustrated in Table I for the case $k = i+2$, $a_i = G$ and $x = T$. In the table, the symbol $\sim$ is used to signify "not," i.e., $\sim T$ may be A, C, or G. Part a of the table shows how an error is introduced into $g_0$, making $g_0$ and $g_1$ inconsistent. Part b shows how this error is detected by the top-down and the bottom-up algorithms. Part c shows that there are 5 single base changes to the inconsistent $g_0$ and $g_1$ which yield consistent sequences. All five cases are different and one of them is the original set of sequences of part a. Thus, the error is detected but cannot be corrected without further information.

The single errors possibilities stemming from an assumed initial error of $g_{01} = \{x, b_j\}$ have been examined. Using an analysis similar to that above the other single error cases can also be catalogued. These are given in Table II along with illustrative examples of each.

Table II, below, provides, a catalog of all of the types of single error substitutions which can occur and an example of each. A $\emptyset$ condition is encountered when either of the indicated string of equalities is broken. The substitution in each example is indicated by a formula such as $x = G > T$ which means that G is substituted for T in either $g_0$ or $g_i$, depending upon in which column the example appears. The symbol "any" means any base (A, C, G, or T).

TABLE I

Single Error Example.

(a) introduce single error into $g_{01}$, $\{G,G\}, -> \{T,G\}$

TABLE Ia

|  | a | b | $g_0$ (0 error) | $g_1$ (0 error) | $g^*_0$ (1 error) | $g_1$ (0 error) |
|---|---|---|---|---|---|---|
| i−2 | $a_{i-2}$ | $b_{i-2}$ | $\{a_{i-2}, b_{i-2}\}$ | $\{a_{i-2}, b_{i-3}\}$ | $\{a_{i-2}, b_{i-2}\}$ | $\{a_{i-2}, b_{i-3}\}$ |
| i−1 | $a_{i-1}$ | $\sim T$ | $\{a_{i-1}, \sim T\}$ | $\{a_{i-2}, b_{i-2}\}$ | $\{a_{i-1}, \sim T\}$ | $\{a_{i-2}, b_{i-2}\}$ |
| i | G | G | $\{G, G\}$ | $\{G, \sim T\}$ | $\{T, G\}$ | $\{G, \sim T\}$ |
| i+1 | T | G | $\{T, G\}$ | $\{T, G\}$ | $\{T, G\}$ | $\{T, G\}$ |
| i+2 | $\sim T$ | $b_{i+2}$ | $\{\sim T, b_{i+2}\}$ | $\{\sim T, G\}$ | $\{\sim T, b_{i+2}\}$ | $\{\sim T, G\}$ |

TABLE I-continued

Single Error Example.

| i+3 | $a_{i+3}$ | $b_{i+3}$ | $\{a_{i+3},b_{i+3}\}$ | $\{a_{i+3},b_{i+2}\}$ | $\{a_{i+3},b_{i+3}\}$ | $\{a_{i+3},b_{i+2}\}$ |
|---|---|---|---|---|---|---| b) sequences deduced from the inconsistent data $g^*_0$ and $g_1$ using top-down and bottom-up recursion relations.

TABLE Ib

| | top-down | | bottom-up | |
|---|---|---|---|---|
| | a | b | a | b |
| i−1 | $a_{i-1}$ | ~T | T | ∅ |
| i | G | T | T | G |
| i+1 | G | T | T | G |
| i+2 | ∅ | | ~T | $b_{i+2}$ | c) the five possible sequences arising from the five possible one error "corrections" to the inconsistent gel data used in part (b).

TABLE Ic

| | $g_{0i}=\{G,G\}$ | | $g_{0i+1}=\{G,G\}$ | | $g_{1i}=\{T,T\}$ | | $g_{1i+1}=\{T,T\}$ | | $g_{1i+2}=\{T,T\}$ | |
|---|---|---|---|---|---|---|---|---|---|---|
| | a | b | a | b | a | b | a | b | a | b |
| i−1 | $a_{i-1}$ | ~T | $a_{i-1}$ | ~T | $a_{i-1}$ | ~T | $a_{i-1}$ | ~T | $a_{i-1}$ | ~T |
| i | G | G | G | T | T | G | G | T | G | T |
| i+1 | T | G | G | G | T | G | T | G | G | T |
| i+2 | ~T | $b_{i+2}$ | ~T | $b_{i+2}$ | ~T | $b_{i+2}$ | ~T | $b_{i+2}$ | ~T | $b_{i+2}$ |

TABLE II

| $g_{0j}=\{x,b_j\}$ | $g_{0j}=\{a_j,y\}$ | $g_{0j}=\{x,b_{j-1}\}$ | $g_{0j}=\{a_{j+1},y\}$ |
|---|---|---|---|
| top-down | | | |
| $a_{j+1}=a_{j+2}=\ldots=$ x; | $a_{j+1}=a_{j+2}=\ldots=$ y; | $a_{j+1}=a_{j+2}=\ldots=$ $a_j$; | $a_{j+1}=a_{j+2}=\ldots=$ $b_j$; |
| $b_{j+1}=b_{j+2}=\ldots=$ $a_j b_j$; | $b_{j+1}=b_{j+2}=\ldots=$ $b_j$; | $b_{j+1}=b_{j+2}=\ldots=$ $b_j=x$; | $b_{j+1}=b_{j+2}=\ldots=$ y; |
| x=G−>TT | any T<−G=y | x=T−>GT | any G<−T=y |
| GT | GT | GT | GT |
| GT | GT | GT | GT |
| . | . | . | . |
| . | . | . | . |
| . | . | . | . |
| $b_{j-1}=b_{j-2}=\ldots=$ x; | $b_{j-1}=b_{j-2}=\ldots=$ y; | $b_{j-1}=b_{j-2}=\ldots=$ $a_j$; | $b_{j-1}=b_{j-2}=\ldots=$ $b_j$; |
| $a_{j-1}=a_{j-2}=\ldots=$ $a_j$; | $a_{j-1}=a_{j-2}=\ldots=$ $a_j=b_j$; | $a_{j-1}=a_{j-2}=\ldots=$ x; | $a_{j-1}=a_{j-2}=\ldots=$ $a_j=y$; |
| . | . | . | . |
| . | . | . | . |
| . | . | . | . |
| TG | TG | TG | TG |
| TG | TG | TG | TG |
| TG | TG | TG | TG |
| x=G−>T any | TT<−G=y | x=T−>G any | TG<−T=y |

EXAMPLE 4

Error analysis when two errors are present and complementarity is not used

When two errors occur on a set of gel data ($g_0$ and $g_1$), there are two separate cases to consider. The first case occurs when the errors are sufficiently far apart to be separately identified. The analysis for this case is essentially identical to that described for single errors. The second case occurs when the errors are sufficiently close to each other such that the two errors "cancel each other out" and thereby go undetected.

An example of the first case arises when $b^*_k=\emptyset$ from the bottom-up algorithm and $b^*_i=\emptyset$ from the top-down algorithm and $k>i$. More than one error is involved since the two partially determined sequences do no overlap. To bridge the gap from one error to the other (assuming only two errors are involved), sequence information between the two errors must be generated. For example, starting with $g_{0k-1}=\{x_{k-1}, y_{k-1}\}$ which has not yet been used by the bottom-up algorithm, either $\{a_{k-1}=x_{k-1}, b_{k-1}=y_{k-1}\}$ or $\{b_{k-1}=x_{k-1}, a_{k-1}=y_{k-1}\}$. The first alternative is tested and the bottom-up algorithm (Equation (7)) is used to determine the sequence up to $b_i$. If ∅ is not encountered, then the choice is correct. If ∅ is encountered, then the second alternative, $\{b_{k-1}=x_{k-1}, a_{k-1}=y_{k-1}\}$ is tested. If this is successful, the two errors have been isolated and the above analysis is independently applicable to both errors.

Considering the opposite extreme, when the two errors occur at the same gel location, i.e., $g^*_{0i}=\{x,y\}$ with $x,y\neq a_i$ and $x,y\neq b_i$ using the top-down algorithm (Equation (5)) $a_1, \ldots, a_i$ and $b_0, \ldots, b_{i-1}$ are correctly determined before encountering $b^*_i=f(a_i, g^*_{0i})=\emptyset$. From the bottom-up algorithm (Equation (7)), $a_n, \ldots, a_{i+1}$ and $b_n, \ldots, b_i$ are correctly determined before encountering $a^*_i=f(b_i, g^*_{0i})=\emptyset$. Combining the partially determined sequences, the entire correct sequences for a and b can be deduced.

EXAMPLE 5

Detection and correction of double errors using a second shift $g_2$

Some double errors are detectable but not correctable using complementarity. Such double errors are corrected by sequencing a second shifted DNA fragment that has a different shift, e.g., two bases, such that $$g_2 = \{\{a_1, b_{-1}\}, \{a_n, b_0\} \ldots, \{a_n, b_{n-2}\}, \{b_{n-1}\}, \{b_n\}\} \quad (26)$$

Now any combination of two gels ($g_0$ and $g_1$, or $g_0$ and $g_2$, or $g_1$ and $g_2$) will produce the a and b sequences.

Starting with the double error example where $g^*_{0j} = \{a_{j+1}, b_j\}$, $g^*_{0j+1} = \{a_j, b_j\}$ with $a_j = b_j \neq a_{j+1}$. The various results are summarized in Table III. If a and b are unrelated sequences, then $g_0$ and $g_1$ indicate no errors; complementarity reveals the errors but cannot correct them. The data $g_1$ and $g_2$ produce sequences with no discernable errors even when complementarity is assumed.

At this point, selection of the result of $g_1$ and $g_2$ over that of $g_0$ and $g_1$ can be made, there $g_1$ and $g_2$ have no indication that there are errors. Confirmation comes from considering a and b derived from $g_0$ and $g_2$. Since the shift is two bases, there are two subsequences, $\{a_1, a_3, \ldots\}$ with $\{b_1, b_3, \ldots\}$ and $\{a_n, a_4, \ldots\}$ with $\{b_2, b_4, \ldots\}$, which are determined independently of each other. The error $g_{0j}$ occurs in one sequence while the error $g_{0j+1}$ occurs in the other. Thus, both subsequences have single errors which are detectable assuming a and b are unrelated and are correctable assuming a and b are complementary. The data $g_0$ and $g_2$ yield the correct sequences also.

Other types of double errors yield similar results. Therefore, double-stranded sequencing data from a second shift allows correction of these errors.

Results for determining sequences a and b using various gel data combinations, when the only errors are $g^*_{0j} = \{a_{j+1}, b_j\}$, $g^*_{0j+1} = \{a_j, b_j\}$ with $a_j = b_j \neq a_{j+1}$ are shown in Table III.

TABLE III

|  | unrelated strands | complementary strands |
|---|---|---|
| $g_0$ and $g_1$ | no errors detected | errors detected |
| $g_1$ and $g_2$ | no errors detected | no errors detected |
| $g_0$ and $g_2$ | two errors detected | both errors detected |

EXAMPLE 6

Computer similation of errors demonstrates that the total number of gel lanes or gel runs needed to achieve a desired level of accuracy can be reduced by up to a factor of two or more.

A computer simulation which introduces random errors into $g_0$ and $g_1$ (and $g_2$) and then uses this gel data with random errors in an attempt to reconstruct the original sequences has been devised. The following simple approach provides an estimate of the error handling capabilities. Given the gel data $g_0$ and $g_1$:

1) The top-down algorithm is applied until $a_k = \emptyset$ or $b_k = \emptyset$ is reached indicating an error has occurred. For definiteness, assume the error occurs at $a_k = \emptyset$. To continue on the top-down path, it is assumed that $g_{ok}$ is correct and that $b_k$ is one of the two bases of $g_{ok}$ (see Equations (3) and (5)). The computer algorithm tries both choices and chooses the one which can proceed the furthest before encountering another $a_k = \emptyset$ or $b_k = \emptyset$ condition. All succeeding $\emptyset$ conditions are handled the same way until the end of the sequences is obtained. The resulting sequences are called $a_{td}$ and $b_{td}$. Both sequences have assigned values for each base except for the isolated occurrences where the $\emptyset$ condition was encountered.

2) Next the bottom-up algorithm is applied until $a_j = \emptyset$ or $b_j = \emptyset$ is reached. In the same manner as above, continuing on the bottom-up path, if $a_j = \emptyset$, it is assumed that $g_{1j}$ is correct and that $b_{j-1}$ is one of the two bases comprising $g_{1j}$ (see Equation (4)). Later errors are treated the same way until the end of both sequences is reached. These sequences are denoted $a_{bu}$ and $b_{bu}$. These two sequences also have assigned values for each base except for the isolated occurrences where the $\emptyset$ condition was encountered.

3) With complementarity, there are four different approximations to the correct strand: $a_{td}$, $a_{bu}$, $b^-_{td}$, and $b^-_{bu}$, in which the superscript $^-$ indicates a complement. The bases of the final sequence is determined by requiring that at least two of the four sequences agree at a given location in the sequence. If no two sequences agree upon a base or if two sequences have one base while the other two have another base, the base at that location is taken to be undetermined.

Computer data was generated by constructing random sequences each 300 base pairs long, determining the gel and shifted gel data for each of these strands, and finally introducing random errors into the gel data at a rate of 1%, 2%, 3% and 4%. For each strand of 300 bases, double strand gels with no shift, a shift of two bases, and a shift of four bases were constructed. The algorithm for three double strands is essentially the same as the one used above, except that there are 12 deduced strands to determine a consensus instead of 4. The twelve strands are: $a_{td;1}$, $a_{bu;1}$, $b^-_{td;1}$, $b^-_{bu;1}$ determined from $g_0$ and $g_1$, and $a_{td;2}$, $a_{bu;2}$, $b^-_{td;2}$, $b^-_{bu;2}$ determined from $g_0$ and $g_2$, and $a_{td;3}$, $a_{bu;3}$, $b^-_{td;3}$, $b^-_{bu;3}$ determined from $g_1$ and $g_2$.

An error rate of p means that there is a probability p that a gel reading $\{a_i, b_j\}$ is incorrect. A random number generator was used to introduce errors randomly but at a given error rate. Errors were introduced by changing a correct reading, for example $\{A,T\}$, to one of the other nine possible readings, each with equal probability. Of particular interest is the percentage of bases which are undetermined and the percentage of bases which are determined incorrectly.

For comparison, the case in which a single strand is repeatedly sequenced a given number of times in the presence of reading errors was also considered. No distinction is made here, for the multiple single strand sequencings, between sequencing a strand and sequencing its complement. Because of the manner in which the errors were introduced, either the strand or its complement provides an equivalent amount of information. For these single-strand cases the percentages of undetermined bases and incorrect bases can be determined analytically.

The error rate formulas for the single-strand sequencing used in FIGS. 3 and 4 are as follows. The probability that a base is read correctly is $p_0$ while the probability that it is one of the three other bases is given by $p_1$, $p_2$, or $p_3$. The various possibilities for a single strand read twice are:

$$p^2_0 \quad (A1)$$

$$2_{p_0 p_1} + 2_{p_0 p_2} + 2_{p_0 p_3} + 2_{p_1 p_2} + 2_{p_1 p_3} + 2_{p_2 p_3} \quad (A2)$$

and $$p^2{}_1 + p^2{}_2 + p^2{}_3 \quad (A3)$$

The term in (A1) is the probability that the base is read correctly on both strands. The expression in (A2) is the probability that a different base reading is obtained for the two strands. The expression in (A3) is the probability that the base is read consistently but incorrectly on both strands. Using the well-known connection between combinations of this type and the binomial theorem, expanding $(p_0+p_1+p_2+p_3)^2=1$ generates all of the above terms and guarantees a total probability of 1. Substituting $p_0=1-p$ and $p_1=p_2=p_3=p/3$ in Equation (A2) results in the formula for determined bases with error rate p:

$$2(1-p) + \frac{2p^2}{3}. \quad (A4)$$

Similarly, the formula for incorrect bases with error rate p is obtained from Equation (A3):

$$\frac{p^2}{3}. \quad (A5)$$

The formulas for n single strands can be generated in a similar fashion by expanding $(p_0+p_1+p_2+p_3)^n=1$. A base at a given location along a strand is considered correctly determined if the correct base is read more often than any other single base is read, among the n strands. In terms of the probabilities this means that $p_0$ occurs more frequently than any of the other $p_i$s. Bases are considered undetermined if no base occurs more frequently than any of the others. Bases are considered incorrect if a particular incorrect base appears the most often among the n readings. With these criteria, the following formulas were generated for 3-6 single strands and used in FIGS. 3 and 4:

3 single strand undetermined bases $$2(1-p)p^2 + \frac{2p^3}{9}; \quad (A6)$$

3 single strand incorrect bases $$(1-p)p^2 + \frac{7p^3}{9}; \quad (A7)$$

4 single strand undetermined bases $$2(1-p)^2 p^2 + \frac{8(1-p)p^3}{9} + \frac{2p^4}{9}; \quad (A8)$$

4 single strand incorrect bases $$\frac{28(1-p)p^3}{9} + \frac{7p^4}{9}; \quad (A9)$$

5 single strand undetermined bases $$\frac{20(1-p)^2 p^3}{3} + \frac{10(1-p)p^4}{9} + \frac{10p^5}{27}; \quad (A10)$$

5 single strand incorrect bases $$\frac{10(1-p)^2 p^3}{9} + \frac{35(1-p)p^4}{9} + \frac{17p^5}{27}; \quad (A11)$$

6 single strand undetermined bases $$\frac{20(1-p)^3 p^3}{9} + 10(1-p)^2 p^4 + \frac{20(1-p)p^5}{9} + \frac{50p^6}{243}; \quad (A12)$$

6 single strand incorrect bases $$5(1-p)^2 p^4 + \frac{34(1-p)p^5}{9} + \frac{193p^6}{243}. \quad (A13)$$

To study the effects of a 1% error rate, 1,700,000 strands containing a total of 510 million bases were generated. For a 2% error rate 660,000 strands were generated and for 3 and 4% error rates 330,000 strands were generated. It was necessary to use more strands for the lower error rates because of the lower incidence of errors. FIG. 3 shows the fraction of undetermined bases versus the error rate for a variety of cases. An undetermined base is one for which there is conflicting data for its identification and no reason to choose one identification over another. The curves labeled 2d are double-stranded sequencings which used two gels: the unshifted gel and the gel shifted by two bases. The curves labeled 3d are double-stranded sequencings which used three gels: the unshifted gel, the gel shifted by two bases, and the gel shifted by four bases. Two different curves are labeled 2d and two different curves are labeled 3d in FIG. 3. These correspond to different error models. The curve represented by equally spaced dashes corresponds to the reading error model described above for which each gel reading has a probability p of being changed to one of the nine other possible readings. The curve represented by unequally spaced dashes is a rough attempt to model the case in which each individual base of a gel reading has a probability p of being incorrect. This was done by using the same computer generated data for undetermined bases but considering them to be the result of an error rate of p/2. Errors of this type are more likely to be due to physical properties of the strands rather than reading errors.

As seen from FIG. 3 sequencing the two double strands compares favorably with sequencing three or four single strands and is dramatically better than the sequencing of two single strands. Sequencing of three double strands is significantly better than or comparable to sequencing of six single strands, depending upon which error model is used.

FIG. 4 shows the fraction of incorrect bases versus the error rate for the same cases discussed above. An incorrect base is one for which there appears to be sufficient data for its identification but, because of errors, the identification is wrong. For the reading error model, the sequencing of two double strands is seen to be comparable to the sequencing of four single strands, for an implied savings of 50% in the required number of sequencings. The double strand sequencing of three strands is better than the sequencing of six single strands, for the reading error model, and lies between the sequencing of five single strands and six single strands for the other error model.

Since modifications will be apparent to those of skill in the art, it is intended that this invention be limited only by the scope of the appended claims.

We claim:

1. A method for simultaneously sequencing both strands of a target double-stranded DNA fragment containing single strands a and b of lengths n and m, respectively, comprising:
   (a) preparing shifted DNA from a portion of said target DNA, wherein:
   strand a is shifted by i bases compared to the a strand of the target DNA and strand b is shifted by k bases compared to the target DNA; and
   $0 \leq |i| < n$ and $0 \leq |k| < m$, except that $k \neq i$;
   (b) simultaneously sequencing both strands of the shifted DNA and simultaneously sequencing both strands of the target DNA to generate a data set $g_0$ of alternative base pairs for the target DNA and a data set $g_1$ of alternative base pairs for the shifted DNA, wherein:

the method of sequencing generates only two alternative bases for each position;

$b^-_{n+1+j} = a_i$;

$b^-_{n+1-i} = a^-_i$;

$g_0 = \{\{a_1, a^-_n\}, \ldots \{a_n, a^-_1\}\}$;

$g_1 = \{\{a_{i+1}, a^-_n\}, \ldots \{a_{i+m}, a^-_{n-m+1}\}\}$;

the jth elements of $g_0$ and $g_1$ are $g_{0j} = \{a_j, a^-_{n+1-j}\}$ and $g_{1j} = \{a_{i+j}, a^-_{n+1-k-j}\}$, respectively; $j = 1$ to $n$; and (c) determining all or a portion of the nucleotide sequence of said target DNA by comparison of $g_0$ with $g_1$ to determine the identity of each $a_j$ by:

(i) comparing $g_{0j}$ with $g^-_{0n+1-j}$ and, if $i+1 \leq j \leq i+m$, with $g_{1j-i}$, and if $n-k \geq j \geq n-m-k+1$, with $g^-_{1n+1-j-k}$, to determine $a_j$, except where $a^-_{n+1-j} = a^-_{n+1-k-j+i}$, wherein:

$g_{0j} = \{a_j, a^-_{n+1-j}\}$;

$g^-_{0n+1-j} = \{a^-_{n+1-j}, a_j\}$;

$g_{1j-i} = \{a_j, a^-_{n+1-k-j+i}\}$; and $g^-_{1n+1-j-k} = \{a^-_{n+1-k-j+i}, a_j\}$;

(ii) where $a^-_{n+1-j} = a^-_{n+1-k-j+i}$ the identity of $a_j$ is determined by first determining the identity of $a^-_{n+1-j}$, or $a^-_{n+1-j-k+i}$ and then performing step (i) to determine the identity of $a_j$, wherein: the identity of $a^-_{n+1-j}$ is determined by comparing $g_{0j}$, $g^-_{0n+1-j}$, $g_{1j-k}$ and $g^-_{1n+1-j-i}$, where $g_{1j-k} = \{a_{1+j-k}, a^-_{n+1-j}\}$ and $g^-_{1n+1-j-i} = \{a^-_{n+1-j}, a_{1+j-k}\}$; and the identity of $a^-_{n+1-j-k+i}$ is determined by comparing $g_{0j+k-i}$, $g^-_{0n+1-j-k+i}$, $g_{1j-i}$, $g^-_{1n+1-j-k}$, where $g_{0j+k-i} = \{a_{j+k-i}, a^-_{n+1-j-k+i}\}$ and $g_{0n+1-j-k+i} = \{a^-_{n+1-j-k+i}, a_{j+k-i}\}$; and (iii) performing steps (i) and (ii) for $j=1$ up to $n$, and, wherein said portion includes more than the part of the target DNA than is included in the shifted DNA.

2. The method of claim 1, wherein the shifted DNA is prepared from the target DNA by the addition or deletion of one or more bases from either or both strands of the target DNA.

3. The method of claim 1, wherein the shifting is effected by sequencing the DNA using two sets of primers, such that at least one of the primers in the second is longer or shorter than the corresponding primer in the first set.

4. The method of claim 1, wherein shifting of the target DNA is effected by increasing or decreasing the length of one of the strands of the target DNA compared to the complementary strand.

5. The method of claim 1, wherein shifting is effected by increasing or decreasing the lengths of both of the strands of the target DNA.

6. The method of claim 1, wherein the shifted DNA is a restriction fragment produced by digesting the target DNA with a restriction enzyme.

7. The method of claim 1, wherein shifting is effected by inserting the target DNA into a plasmid vector and using oligonucleotides complementary to the sequences that flank the inserted DNA to prime DNA synthesis when sequencing the shifted DNA, wherein the oligonucleotides that are complementary to each flanking sequence are of different lengths.

8. The method of claim 1, wherein:

prior to preparing the shifted DNA, the target DNA is inserted into a plasmid vector and shifting is effected by priming each sequencing reaction with oligonucleotides complementary to sequences that flank the inserted DNA when both strands are simultaneously sequenced;

the oligonucleotides in the second sequencing reaction that are complementary to each flanking sequence differ in length by l nucleotides;

l is greater than or equal to 1; and the oligonucleotides used to prime the first sequencing reaction are of identical lengths or of different lengths, but do not differ by l.

9. The method of claim 1, wherein prior to preparing shifted DNA from a portion of said target DNA, the DNA is amplified by attaching tails to the ends of the target DNA and amplifying the DNA with attached tails using oligonucleotides complementary to the added tails as primer for DNA synthesis, wherein the tails are selected from the group consisting of tails that have sequences of nucleic acids that are same whether oriented 3' to 5' or 5' to 3'.

10. The method of claim 9, wherein said tails are selected from the group consisting of DNA fragments that are homopolymers and DNA fragments that have sequences that are palindromes.

11. The method of claim 9, wherein said tail has a nucleotide sequence that is a palindrome.

12. The method of claim 9, wherein the tail is a homopolymer and is attached to the target DNA by chain extension using T4 terminal transferase to add nucleotides to the 3' termini of the target DNA, followed by annealing oligonucleotides complementary to said added nucleotides and ligating said annealed oligonucleotides to the target DNA.

13. The method of claim 12, further comprising treating the resulting tailed target DNA fragments with S1 nuclease.

14. The method of claim 1, further comprising:

(d) shifting the target DNA to produce another shifted DNA fragment, wherein the other shifted DNA is different from the first shifted DNA molecule;

(e) repeating this shifting step n times;

(f) simultaneously sequencing both strands of each of the other shifted double-stranded DNA fragment(s) to produce gel data $g_n$ for each shifted DNA fragment; and (g) comparing gel data $g_0$ with gel data $g_n$ or gel data $g_n$ with gel data $g_{n+1}$; whereby sequencing errors are corrected, wherein n is an integer greater than or equal to one and less than or equal to the number of repeats of steps (a)-(g) to detect and correct all sequencing errors.

15. The method of claim 1, wherein: $i=0$, $k=1$ and the identity of at least one base is known.

16. A method for simultaneously sequencing both strands of a target double-stranded DNA fragment containing single strands a and b of lengths n and m, respectively, comprising:

(a) preparing shifted DNA from a portion of said target DNA, wherein the length of strand a of the resulting shifted DNA is $n+i$ and the length of strand b is m, wherein $0 < |i| < n$;

(b) simultaneously sequencing both strands of the shifted DNA and simultaneously sequencing both strands of the target DNA to generate a data set $g_0$ of alternative base pairs for the target DNA and a data set $g_1$ of alternative base pairs for the shifted DNA, wherein:

$b^-_{n+1+j}=a_i$;
$b^-_{n+1-i}=a^-_i$;
$g_0=\{\{a_1, a_{-n}\}, \ldots \{a_n, a^-_1\}\}$;
$g_1=\{\{a_{i+1}, a^-_n\}, \ldots \}\}$;
the jth elements of $g_0$ and $g_1$ are $g_{0j}=\{a_j, a^-_{n+1-j}\}$ and $g_{1j}=\{a_{i+j}, a^-_{n+1-j}\}$, respectively; and j=1 to n, for i>0, and j=1 to n+i for i<0

(c) determining all or a portion of the nucleotide sequence of said target DNA by comparison of the jth element of $g_0$ with $g_1$ for j=1 to n.

17. The method of claim 16, wherein i=1.

18. The method of claim 16, wherein at least one base on either strand is known.

* * * * *

UNITED STATES PATENT AND TRADEMARK OFFICE
CERTIFICATE OF CORRECTION

PATENT NO. : 5,308,751
DATED : May 3, 1994
INVENTOR(S) : Ohkawa, et al

It is certified that error appears in the above-indentified patent and that said Letters Patent is hereby corrected as shown below:

IN THE CLAIMS: Column 37, Claim 16, lines 4, 5 and 6 should read:

-- $b^-_{n+1-i} = a^-_i;$
$g_0 = \{\{a_1, a^-_n\}, \ldots \{a_n, a^-_1\}\};$
$g_1 = \{\{a_{i+1}, a^-_n\}, \ldots \{a_{i+m}, a^-_{n-m+1}\}\}$ Signed and Sealed this Sixth Day of September, 1994

Attest:

BRUCE LEHMAN

*Attesting Officer*     *Commissioner of Patents and Trademarks*